(12) United States Patent
Jiang et al.

(10) Patent No.: US 7,879,552 B2
(45) Date of Patent: Feb. 1, 2011

(54) **ASSOCIATION OF *UQCRC1* SNPS WITH FAT DEPOSITION AND FATTY ACID COMPOSITION**

(75) Inventors: Zhihua Jiang, Pullman, WA (US); Jennifer J. Michal, Albion, WA (US); Tanja Kunej, Ljubljana (SI)

(73) Assignee: Washington State University Research Foundation, Pullman, WA (US)

( * ) Notice: Subject to any disclaimer, the term of this patent is extended or adjusted under 35 U.S.C. 154(b) by 1 day.

(21) Appl. No.: 12/125,968

(22) Filed: May 23, 2008

(65) Prior Publication Data

US 2009/0092978 A1 Apr. 9, 2009

Related U.S. Application Data

(60) Provisional application No. 60/939,715, filed on May 23, 2007.

(51) Int. Cl.
  *C12Q 1/68* (2006.01)
  *C12P 19/34* (2006.01)
  *C07H 21/02* (2006.01)

(52) U.S. Cl. .......................... 435/6; 435/91.2; 536/23.1

(58) Field of Classification Search ........................ None
See application file for complete search history.

(56) References Cited

U.S. PATENT DOCUMENTS

2007/0020658 A1   1/2007   Jiang

OTHER PUBLICATIONS

Juppner H. Bone (Aug. 1995) vol. 17, No. 2, Supplement pp. 39S-42S.*
Hacker U.T. et al. Gut (May 1997), Vo. 40, No. 5, pp. 623-627.*
Schmid et al., Effect of high-fat diet on the expression of proteins in muscle, adipose tissues, and liver of C57BL/6 mice, 2004, Proteomics, vol. 4, No. 8, pp. 2270-2282 (p. 2273, col. 1, para 1; p. 2278, col. 2, para 2).
UQCRC1—SNP Results, ENTREZ SNP [online]. [Retrieved on Sep. 2, 2008]. Retrieved from the internet: <URL: http://www.ncbi.nlm.nih.gov/sites/entrez.
AAFC03053028.1, ENTREZ NUCLEOTIDE [online]. [Retrieved on Sep. 2, 2008]. Retrieved from the internet: <URL: http://www.ncbi.nlm.nih.gov/entrez/viewerfcgi?db=nuccore&id=112125286.

* cited by examiner

*Primary Examiner*—Stephen Kapushoc
(74) *Attorney, Agent, or Firm*—Judy Jarecki-Black; Chad Kitchen; Merial Limited

(57) ABSTRACT

The present invention relates to the identification of single nucleotide polymorphisms (SNPs) in a ubiquinol-cytochrome c reductase core protein I (UQCRC1) gene and its associations association with fat deposition and fatty acid composition. The invention further encompasses methods and systems, including network-based processes, to manage the SNP data, haplotype data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

2 Claims, 12 Drawing Sheets

Promoter Polymorphisms

```
ATTCCCAAGTGGCTCAGTGGGTAAAGAATCCACCTACAATGCAGGAGATATGGGTTCAATCCCTGGGTCAGGAAG
ATCCCCTGGAGGAGGAAATGGCAACCAGTCCAGTATTCTTGCCTGGAAAATCCCAGTAACAGAAGAGCCTGGTGG
GCTCCAGTCCATGTGGTTGCAAAGAGTCGGACACGACTGAAATGACTGCGCACGCACGCACGCACACTGCTGGAA
GGAAGGTACACCGGAAGGAATTGTGTCACAGCAAGAGGAGCCTAAGAAAACACGACAGTGAAACGTAATGTGGTG
TCCTGGACAGGATCCTAGAACAAAAAAGGCCATTAGATGAAAACCAACTAAGGGAATCTGAATAAACTATGAAGT
CAAAGTCGCTCTGTCATGTCCGACTCTTTGTGACCCCACGGACTATACAGTCCATGGAATTCTCCAGGCCAGAAT
ACTGGAGTGGGTAGTCTTTCCTTTCTCCAGGGTATCTTCCCAACCCAGGGATGGATCCCAGGTCTCCCACAGGCA
GATTCTTTACCAGCTGAGCCCCAAGGGAAGTCCAAGAATTTTGCACTTTAGAAATAATAAATGTGTCAATACTGA
TTCATTAATTGTAACAAAGTTATCAGAATAAGGTAAGATATTAATAAGGCAAATTGTGCATGGCTGTATGTGGGC
AGGTATATATGGGAAATTCTGTACTTTCTGCTCAGATTTTCTGTAAATATAAAATGGTTCTAAACACCAGTAATT
AAAAAAACTGTACTAAAAAACTAGGAGATTCTATTTCACTGTATTTTTCATGTCTAGATGATAACGTCATTTTAG
TTCACAAGATATTAATCAATGCACACTTAAGCATCATCTCTTTGATGTTTAACATAATTTTGTTTATTTTTGGCT
GTGTTGTGTCTTCTTTGCTGTATGGATTTTCTCTAGCTGCAGTGAGCCAGGCTGCTCCTCCTCGAGGTGCTCGGG
CCTCTCGTTGTGGTGATGCTCTCTTGTTGCAGAGCAGGGGCTCTAGGGTGTGGGGCTTCAATAGTTGTGGCACA
AGGGCTCTAGAGCAGAGGCTCAATAGTTGTGGTTCAGTTCAGTTCAGTTCAGTCTCTCAGGTGTGTCCGACTCTT
TGCAACCCCATGAATCACAGCACGCCAGGCCTCCCTGTCCATCACCATCTCCCAGAGTTCACTCAAACTCACATC
CATCGAGTCAGTGATGCCATCCAGCCATCTCATCCTCTGTCGTCCCCTCTTCCTCCTGCCCCAATCCCTCCCAT
CATCAGAGTCTTTTCCAATGAGTCAACTCTTTGCATGAGGTGGCCAAAGTGCTGGAATTTCAGCTTTAGCATCAT
TCCTTCCAAAGAAATCCCAGGGCTGATCTCCTTTAGAATAGACTGGTTGGATCTCCTTGCAGTCCAAGGGACTCT
CAAGAGATGGGCTTAATTGCTCTTTGGCATGTGGGATCTTCCCAGATGAGGTTTCAAACCGGTGTCTTCTGGACT
GGCAGGTGGATTCTTTACCAGTGAGCCACCAGGGAAGCCCCTTCTGTTTCATTTTCATAAAAGAAAGTTCTATTT
TCATTGAGCGATATTTTGAAAGGTCACAAAAAATCTCATATATCTGTAAAAGGAAGTTCAGTTCAGAAATATGCC
ATTATTTCAAAAGCAACAAATACTTTTAATAAAAGTTTTATTTTACTTTTTTTTTTTTTAATTTCTGGCCATG
CACAGTGGCTTGTAGGATCTTAGTTACCCAACCAGGGATTGAATCCCAGCCACTGCAGTGAAAGCACCGAGTCCT
AGCCACTGGACTGCCAGAGAATTCCCTAAAAATTTAAAATCATGTATTAAAATAAAACAGAAGTGTGAAAATGGT
AGCCTCTTTCCCCTTCCCCTGAATTTATTTTCTGTAAGTCATCTGACTGAGACTTTACAGTGAGTTCCTAGGAAT
TCTCTGTTGCCTATGCAAGTCCTCTTGATGTGTGTTTTGTTTTCCAAACAAGGAATCTTTTCCACAAATTAGTCT
CTAAAATTGTTCCTTTTTTCTTAGCAACACATTGCTAAATTCTTTCCATGTTAACCATCTGAATTTACTCCGTTC
CTTTAAAAAGAAGACCGTGACTTTTCAACAGCCGCCCAGCCGTCCTAGGTTCCAGCCTGGTACTTTAGCCCTGGG
GGTGATAGAATTCCAGTTGAGCTATTTCAAATCCTGAAGGATGATGCTGTGAAAGTGCTGCACTCAATATGCCAG
CAAATTTGGAAAACTCAGCAGTGGCCACAAGACTGGAAAAGGTCAGTTTTCATTCCAATCCCAAAGAAAGGCAAT
GCCAAAGAATGCTCAAACTACCGCACAATTGCACTCATCTCACACGCTAGTAAAGTAATGCTCAAAATTCTCCAA
GCCAGGCTTCAGCAATACGTGAACCATGAACTTCCTGATGTTCAAGCTGGTTTTAGAAAAGGCAGAGGAACCAGA
GATCAAATTGCCAACATCGGCTGGATCATGGAAAAAGCAAGAGAGTTCCAGAAAAACATCTATTTCTGCTTTATT
GACTGTGCCAAAGCCTTTGACTGTGTGGATCACAATAAACTGTGGAAAATTCTTCAAGAGATGGGAATACCAGAC
CACCTGACCTGCCTCTTGAGAAATTTGTATGCAGGTCAGGAAGCAACAGCTAGAACTGGACATGGAACAGACTGG
TTCCAAATAGGAAAAGGAGTACGGCAAGGCTGTATATTGTCACCCTGTTTATTTAACTTATATGCAGAGTACATC
ATGAGAAACGCTGGGCTGGAAGAAACACAAGCTGGAATCAAGATTGCCGGGAGAAATATCAATAACCTCAGATAT
GCAGATGACACCACCCTTATGGCAGAAAGTGAAGAGGAACTCAAAAGCCTCTTGATGAAAGTGAAAGTGGAGAGT
GAACAAGTTGGCTTAAAGCGCAACATTGAGAAAATGAAGATCATGGCATCCGGTCCCATCACTTCATGGGAAATA
GACGGGGAAACAGTGGAAACAGTGTCAGACTTTATTTTTCTGGGCTCCAAAATCACTACAGATGGTGACTGCAGC
CATGAAATTAAAGGACGCTTACTCTTGGAAGGAAAGTTATGACCAACCTAGATAGCATATTCAAAAGCAGAGACA
TTACTTTGCCAACAAAGGTTCGTCTAGTCAAGGCTATGGTTTTTCCTGTGGTCATATATGGATGAGAGAGTTGGA
CTGTGAAGAAGGCTGAGCGCCAAAGAATTGATGCTTTTGAACTGTGGTGTTGGAGAAGACTCTTGAGAGTCCCTT
GGACTGCAAGGAGATCCAACCAGTCCATTCTGAAGGAGATCAGCCCTGGGATTTCTTTGGAAGGAATGATGCTAA
AGCTGAAACTCCAGTACTTTGGCCACCTCATGCGAACAGTTGACTCATTGGAAAAGACTCTGATGCTGGGAGGGA
TTGGGGGCAAGAGAGGAGAAGGGGACGACAGAGGATGAGATGGCTGGATGGCATCACTGACTCGATGGACATGAG
TCTGAGTGAACTTCGGGAGTTGGTGATGGACAGGGAGGCCTGGCGTGCTGCGGTTCATGGGGTCGCAAAGAGTCG
GACACGACTAAGCGACTGATCTGATCTGATCTGCGGTTCGCAAACATGCTGTGCTTGCGCTTCCGGCCCGCTCGC
CCACTCCAAGCACTCAGTGCAGTCGAGGCGCCCACGGTTCGTGAGAAACGTCGGGCACTCTCCCACGAGTGAAGG
GGAAAGATGAACTGGATGCAGAACAGATCTGAGCAGGACGATGACTAGCCAGGGGCATTGATGCGCGCTGGTACC
CAGGGACGCGAAGACAAGAAGCAGCGACCTTCAGGGAGTAAGTGAATTTTTCCGGTCTCCTCCGCCAGGGGCGAG
CCGAGCGCCAAGACCCCAGTACTGCGCCTGCCCTCGCGCCTCTACGCATGCGTGGCGCGGCCCAGCGTCCACTG
GAGCTTAGAAGATGGCGGCTTCCGCTGTTTGCCGGGCAGCTGGCGCCGGGACGCGAGTGCTGCTACGCACCCGCC
GCTCGGTGAGGTGGCAACGAGAGCGCAGAGCTGTGGGAAGCGGGGCTTCGGAACGCGGACCGGGAGCGGGCTGTT
AGTGCCCGTGGAGAATGGGGAGGTCGCGGGGTCAGGGCCGTGGGAAGGTCACGGCCCAGGGCGCGAACGGGAGTC
```

FIG. 3A

```
TCGTAGACCGCCTGAGCACGGGGACGGGGATCCCACACTGCAGGCCTGCAAGCTGAGGCGTGACCCCCTACTCTA
GTCCTCAGTCCCGGTCGCCTTTTTCCAACAGCCGGCCCTGCTGAGGTCGTCTGACTTGAGGGGCACCGCCACCTA
CGCCCAGGCTCTCCAGAGCGTGCCAGAGACGCAGGTCAGCCAGCTGGACAACGGGCTGCGAGTGGCCTCGGAGCA
GTCTTCCCAGCCTACCTGCACGGTGAGCGGAGTCCGCTGTCAGGAGGGCGCCTCCATGTTGGGCACGGCCTCCTT
TCCCAGGTCGGGGTGTGACCTTGGGCTCTATGTTTGGGTCAGACTCTCCTCAGTCACCCTGAGGATTGACCCTC
CTACTCCAGTCGCGATTCTAACCATGCCTTGACTTCGTGGAGGCAGTTCTCACTAAACCAACACTCATTTAGCAT
GTGATGCCTGCCAATCAGGAGGCCAACCCCCTTTTCAGCTTTTTCTTTAGCAGCCCATGGGATTCAGAGACTTAG
ATGACTGCCAGCCTCATGGCCCAAACTTGTAATCCCTTGGCTAGATTGGAAATGTATTGCAAAAGAAAACCACGT
GAAAATTCCAGTTAAATGGATAATTTTCCTGAAGATTGGCTCAAAGATAGATATCTTGGTTAGGTAAACAGGAGA
GAAGATTCTCAAGAGGCGATCTCTCTCTCTCATTCCACCCCCACCCCCTCTCCAAGTGGTTTGATTGGTAAAT
TCTTTGAGTTTTCCAGGAATAATGTCCTGTGATGCAAGTTGTGACTGAACACCGCAAAAAGTGATGGGTAGCTTT
CTTCCTACATGACACCTGTATAAGCTGACACACAGCCTGTTAAGAAAACTTGACCGAGAATGCTGTATTTCATGG
ACACTAAGATGCCCAGGGCTTCCCAGGTGGCTCAGTGGCAAAAGAACCCACCTGCTAATACAGGAGACACAAGAG
AAATGGGTTTGATCCCTGGGTCGGGAAGATCCCTTGGAGAAGGAAATGGCAACACACTGTGGAATTCTTGCCTGG
GACATCCCATGGCAGAGGAGCCTGGCAGGCTACAGTCCATGGGGTCACAAAGAGTCGGATGCGACTTAGCGACTG
AGAGCAAAAATGAAACAAAAGATGCCCTTGATCTTAAGGAGCACCACTGTGCTCAATTGCCAGAGAAAGAATGCT
GCCAGTTGTAGTCAAGGAATACTATGGATTACAAAATGCATCTGTTGAAGGTGTTAGATGGGTAGTAGATGATGT
TCATGTAAGAATTTATGGTATATAGGACATACATGAACGTCTCTTAGTAAAGCAGATGTGAGCATTTTAAATCAG
CTACGATACAAATAGTAGAAGATTAGATCTGTGTTACCATGGGGGTGAGTAGTGTGATGTGCATTTCACAGCACA
CAAGGAAGCTATTACAATTATAAGAATCTCTCATTGGGTGCCAAGGTGCGTTGGCAGTGTTAGGTGTCCAGGTCT
GATTAAAAAGATTTTTTAAGTATGAATGAGCCTCCTCCTTTAATGGCGAAAGAACGCAATCTCCAGGACAAAAAG
ACAGGGTGTAATTTTTAGGAAGGAGAAAAAAAGTTGTTTGCAAGTGATTAGTAGTTTGCCGAGAAGAAACAAAGA
ATCAACTGAAAAGTGAGACTGAATTTAAGAATTTTCTGCAGTGATGGGACAGGTGAATGTGCAGTTAGAAGCTTT
CCTGGAAGTCTCGTCACCAGCAGAAACCAGAGCAGGGATTAGAGGTGATGCAGTGTGACTAGTCAGTCAGCTGGC
ACCCGAGCGTCCGACCTCGGGGCCTTCTGAGAACGTCTTCCCCACCTGGAACCGTGAGCCCCTGTCTGGGGCTTG
TTCTGGATCCTGCAGGGTCAGGTGTGAGTGGGGGCTGGTGTCTGTTTCTTTATTACCTTTTTTGGTGATTTCTTG
TCCAGGTGGGGGTATGGATTGATGCTGGCAGCCGTTACGAGACTGAGAAGAACAACGGGGCTGGCTACTTTGTGG
AGCATCTGGCTTTCAAGGTGAGGCTCCTAAAGTCCTGCATCTCCCCTGTACTGAGGGCTTCCTGCTGTCCCTCCT
GAGTATGCTGGTCAGAAAAGTTAGCCTCCTCACTTAGGACTGTTAGCAAGGGGGCAGAGGGAAGCGATCTCTGTC
TGGCTTTCCTGGGAGACGCCACGTGGGCCAGGCCTCTCCTGAGTGAGTGCCTACCTGGTAAACCCCTGCACAAGG
TCCCCAGAGCCAGAAAAACCCCAAGGAGCATGGGAGCCCTGCTCTTCACCAGAAGCCAGGCCTGTGTTGTTTGTC
TGCACGGACGTAGAATTGCGGATGTACACATGCATTGTAACAAGTCCAGCAACTTAGTTTTTGTAAAATGCTGTG
TATCTCTGACTTGTAAAATCGAGTAGGAGCTTTCATGAGGATGAGAACAACCCCTTAGCCATCCTGTGTTTGCAT
GGAGTAAACAATGAGTTTCTAAACGAATGAAAAAAATAGAGACGATACAGGGTTGGTGAGGGTGTGGAGCAGGAA
TGGGCAGCTAGCCAGCTCCAGCGTCACAGATGTGTGTCAGTCTCAGCACGTGGGTGTGTCATTGGACAGCA
GTTCTCACACACACACGCAGGACGAAGGCTGAGCCCCACAGAGGCCCCTGGCACACACACAGTCATACATG
GTGTGAGGGAGAGTGGGGAGCAGCGTCGCCTGAGCACAGTGTGAGTCCACCTGACCACGGCTGTCAGTAAGCGTG
GGCTGGTGAGGTCAGGCTGCCGTGGGCGCTCTGCAGTCACATGCGCTCCCCCGAGCTGTCCCCCCTCTTGGTGTG
GGGGTGCTGGATTTCTGGTAACACTTTTGGGCATGCCCTTCTTCCCTGGCCCCTGGATGTCTCCATTCTGTCGGG
CCACGGTGCTGTGGCCTTGAGGAGCTTAAGGCCTACTGAGCACTTGGTGGCCCCAGACTCTGGGCCCTGCACCCC
AGAGTCTTTGCTGAGGGCGCTACCTGTGGACCAGTGGTCCTGCTGGGACTTCAGCCTATGAGGATGCAGGATCTT
GGGCTCCCATGTGGCTGGTTCCAGGGAACAAAGAATCGGCCTGGCAATGCCTTGGAGAAGGAGGTGGAGAGCATG
GGGGCCCATCTTAATGCCTACAGCACCCGGGAGCACACGGCTTACTACATTAAGGCGTTATCAAAGGACTTGCCA
AAAGGTAAGCCTGGAGGGCAGGGCTGGCATGCGGTAGGACTCCCGGGTGCAGAGGACAGGCGCTCAGGAGCCCC
TGGCCTGACTGAAGAATGGGGTGACCCTTAGAGAAGAGCCTTGACACCAAGGGGGTCAGGCCTGGGGGTTTATG
CTGTTACTGTCTCCACACCTGTCCTCCTTGCACCCAGCTGTAGAGCTCCTGGCCGACATCGTGCAGAACTGCAGC
CTCGAGGACTCCCAGATTGAGAAGGAGCGGGACGTGATCCTGCAGGAGCTGCAGGAGAATGACACATCCATGCGG
GACGTGGTCTTCAACTACCTGCATGCCACGGCCTTCCAGGGCACACCTCTAGCCCAGTCCGTGGAGGGGCCCAGT
GAGAATGTCAGGTGCGAGCTGGCTGGTCCAGGGGCAGGTTGTCCCCTTATTGGGGCCTGAGCAGGCCACAGCCG
CAGGAGTTTGCATTTACTTGGCCAAGTGCCTGTGCTGTTTATTTTCTTAATTCACACAACTGGAGACATTTTCTG
TGTTGCCACATGTTCCCCAGGAGTCTTTGAATGTTTGTGTGGTCCCCACTCAAATTGTGGGCTTTGTTTCCATGT
GTGTGTCTTACGGGTGCTCTGGGGGGGTCCCTCCACGTGGCTGCTTGTCCTCTGGTAGGAGGAGCCCTGCCGCTG
CCCCTGAAGCCCCATGTCAGCCCACACCCTCCTTGGAGGGGACTCCAAGCCTATCCTGAAGTTGGACGTGAGAG
GCCCCAGTGAGGGCTGCCCTCTTGGCCCCAGAGTGGCAAGTGCCAGAGATGGGCAAGGATCCGGTGAAGCTGAG
TCTCCTTGTCTGTCTCCTCCGCCCCATTTTGTGTGACCCGCATCACTGCGGTCTGGGAGCAGTGTTGACCCCTTG
GCGGTGTGTCTTGCAGGAAGCTGTCGCGGGCAGACCTGACCGAGTACCTCAGCCGGCATTACAAGGCCCCCCGAA
```

FIG. 3B

```
TGGTGTTAGCAGCAGCTGGAGGTGAGCAGTGGGCTGGTTGAAGCCCTGTGGTAATGGGGGGGTGGGCTGGGCTGG
GCTGCAACCTTGATTAGCAGGGCCAGGTCTCCTGGTTCTGACTGTGGGGGATCTTCCATTCCTGTGGACCCTGTT
CCCTCCCTGTCCTGTCCTTGAGGGGCGTGACCTCCGTCCTGTGCTCTCTGAGGTGGGGTGGGATTCTGCTGGGCC
ACCTGGGGCTGCTGCTCGCGTTTCATGCACGCCTCAGTTGGCCTGCTGACCTCTGCAGGCCTCAGGACTTTCTCA
GCCTCACCTGGTCCTTGGAGACGAAGGTTGAGGCTGGGGGAGATTCAGGCCTCCAGCCTGTTCCTCTTGGCCTAT
GTGGGAAACCGGACGTCGAATGGTAGATGGAAAGTGCCCCGAAAGGAAGGCACGGTGTGGTCAGGGGATTTTTGT
GGGGGACTCAGAGGTTAGGGTGGAGAAGGCAGTGGCACCCTACTCAAGTACTCTTGCCTGGAAAATCCCATGGAT
GGAGGAGTCTGGTAGGCTACAGTCCATGGGGTCGCTAAGAGTTGGACACGACTGAGCGACTTCACTTTCACTTTT
CACTTCCATGCATTGGAGAAGGAAATGGCCACCTACTCCAGTGTTCTTGCGTGTAGAATCCCAGGGACGGGGGAG
CCGGTGGGCTGCCATCTGTGGGGTCGCACAGAGTTGGACACGACTGAAAGCAGCAGCAGAGGTTAGGGAGGTGCT
TTTGAAGTACTTGTCATTTGAACAGAGAGCTGAAGAGTGGTGGGATTTAGTTACATGGGGAGCGGGGGGTCTGCA
CGGAGGGGCAGAGTGGTGTCACGGGCTCTGTGATTGGAGGCTTGCTCTGCTGCCATGTGGGCTTCCCTGGTGGCT
CCGCTGTAATGAATCCACCTGCCAGTGCAGGAGACGCAGGTTTGATCCTTGGGTCAAGAAGATCCCTGGAGAAG
GAAATGCAGCCCACCCCAGTATTCGTGCCTGAAAAAATCCCATGGACACAGAAGCCTGGTGGGCTACAGTCCATG
GAGTCGCAGAGTTGGACACAACTTAGCAACTGAACAACAGCAGCTGCTGCCATGTCGGGCCAGAGCGGAAGCAG
GTGGATGCAGGGAGGGCTTGTGGCAGGTGCCTGGTGGGAGGCGGCAGGAGGAAGAGAAGCGGATGAACTCGAAAC
GGGTTTGTAGATGGAAGCCTGATAGACATCTAGCCAGGAGGGGACAGGAGCGGGTCAGGGATGCCGCCCCAACTT
ACGGCAGCTGGCTGGACGGGAGAGACTGATAGGAGGAGCTCGGCTGGTGACCTTGGGGCTAGTGAACCAAGAGCA
GTTTGAGCTCCTGACACATCAGACCTGCAGGATCTGAGGTCAAGGAAGGAAAGAATAAAAGGCAGAGGCACCTGG
CGGCCTGTACCTGGGGCGCTGCTTCCTACCACAGCACCCACTGGTCGAGGGGCTGGGGCAGCGGAAGCCGCTGG
TGGAGGGGAGGTCCAGCAAGGGCATGAGACGTGAGTTTGTGACATTGCTGCTCCATGTCCCTGGCACAGGGGCC
CCAGAGCTAGTCACAGCCCCGCGTGGCGCTTCTTTGTGCCCTCTCACCTGCCAGCCCTACAGAATCTGCTTGAGG
AAGGGCTGGAGGGGCGAGGCAGGACGGGTGGCCTCACGCCCAGGGCACCAGTCTTGTGTGGTGCTGGTGAGAG
TGCGTCACGTGCTTCAGCCCGGCGTGTGCTGCTTCCTCATGGCCGAGGTGGTGGGAGCTGTTGGGCCCTGGGGGT
CTGCCCTGCCTGCCGCCGAGCTGGAGTGAGTCTGTGGAGGCTCCTCTTCCCTCACCTGGTCCTGATGTCCTGTCT
TGGGGGTTCTCCCATCGAGGCAGGACATGGGGTCCTGCGCCTCTGTGTGGCGTCTCAGGCCCGGCTGACCGATAA
GCACGCTGTCCATCTCGGCAGGGCTGGAGCACCGGCAGCTGCTCGACCTTGCCCAGAAGCACTTCAGCGGGCTCT
CCGGGACATACGACGAGGACGCTGTGCCTACCCTCAGTCCGTGCCGCTTCACTGGCAGTCAGGTGGGTGGGGGTG
GGTGGGGGTGGCACTCCCGCGGGCCTGGCTCTTTCACGACTCCGGAGGTGCCTCGGAAGTTGGGCCGGGGTCCCG
CGCCTGCTGCCTCCCAGGCACACGTGGTGACGCTCGCATGCACATGCCCCCAGCCACACTTGGCACCTTTGCTGT
CGCCAGGGCGGTCTGGCTGTTCCTCAGCTTTGCCACGTCCCGTTTCAGATCTGCCACCGTGAGGACGGCCTGCCT
CTGGCCCACGTGGCCATCGCAGTGGAGGGGCCTGGCTGGGCCCACCCGGACAACGTGGCCCTCCAGGTGGCCAAC
GCCATCATTGGCCACTACGACTGCACCTACGGTGGCGGAGCGGTGAGTGGGCCAGGCGGGGACCTCGGTTCAGGG
GAGAGGCGCAGCTGGGCGGCGGGCGGGGACCTCAGTTCAGGGGAGAGGCGCAGCTGGGCGGCAGGCGCTCATCCT
GCGGGGTTCGGGGGCAGGTGGCAGAGAGGAGGGCAGGTGCTGACCACCCTGGCCCCTGGTAGCACCTGTCCAGCC
CACTGGCTTCCATTGCTGCGACCAACAAGCTGTGCCAGAGTTTCCAGACCTTCAACATCTGCTACGCAGACACCG
GGCTGCTGGGCGCACACTTCGTCTGCGACCACATGAGCATCGACGACATGATGTTCGTCCTGCAGGGCCAGTGGT
GAGTGGCGGCCGCTGTTGCTGGCCCCGGCGGGCGGGAGGCTTGGGGACCGCAGCGTCTCTCAGGATGACGCGCAC
CTGCCCCTGCCCTAGGATGCGCCTGTGCACCAGTGCCACAGAGAGTGAGGTGCTCCGGGCAAAAACCTCCTCCG
AAACGCCTTGGTGTCTCATCTGGATGGTGAGTCCTGCAGCCCTGTGGCGAGGGGTGGGGTGCGTACGGGCAGTGA
CAGTCCCAGCTCGACCAGTGCTCCTGACCAAGACCGGCAAGGATGACGTTGGCGGTCACATCGTGTCCCACCACT
GCCCCTTCCCCAGGGGCCTGGGGTTTCAGGGACCCCTTGTGGGTGGGCCTGAGAAGCCCATGGGTACAGGTCAGG
TTGCACAGATGAAGATTGTGGTCTAGGATCAGGCCGAGTCAGCACAGAACCCTGGAGGTTCGGTGCGGGCCTGTG
AGCTTCCCTCCCCCTCGTAGGCACCACTCCCGTGTGTGAGGACATCGGACGCAGTCTCCTGACGTACGGCCGCCG
CATCCCCCTGGCCGAGTGGGAAAGCCGGATTGCGGTAACAGGGCCCTGGGGGGAGAGGGCTTTGGGAGTCTTGAG
CTGGCTGACTTGCAGAGGGTGGGGCGTTGAGGCAGACTGCTCCTGTGGGCGCCCCAGGGTGTAACCGGGGGCAG
GGCAGAGGCGTGGGTGGCTGTGGGGTGCCTGGGGCCCGTGGAAGCCTGTGGCCGGGGAGCCCTGCCGCTGTTCCC
CTTTCGGGTGCGGGGTCAGCCCCTCGGTGCGTGGGGCGGTCTTGGTCGCTGGATGCTGTTGACTGGTCCCCAGGG
GCCTTGCCACTCATTGTGCCCTCTGCGTCATCCTGTAGGAGGTGGACGCCAGGTGGTGCGTGAGGTCTGCTCCA
AGTACTTCTACGACCAGTGCCCGGCAGTGGCTGGATTTGGTGAGTAGCCGCTCTCTGGCCGCCTCCTCAGGCTGC
TGTCTGGGCCTCCCATCTGCCTCTGCTTTCCCCCTTCCCCCAACTTTCATTGGGAGCAGCAAGTTGGGCCCCCA
AGAGGCTCTGCCCAACTGCCTGGCTGCCAGGGAGTTCTTGCTCAGAAAACCTGTCCTGGCAGCTCCCTGACTCCC
TGCCAAGGTGCCTCCATCAATACCCCACACCCGCCAGGTAACGGACACCTCCGCATGTGGGGTGGGGCTCCAGAG
GCCAGAGCGTGAAGGGGCAGGCTCAGCACCCCTGGAGGAATGTTCTTTACCCTCTTTCCACTAAAGCCTGCCTT
GTGCTGCTCTGGGCAGCTCTGAATGGGGCGCGGCGCGGGGCCAGGTGTCCCTGTACCACACAGGTGCCCCACCCT
GACGCCCCACCCTCTCCCCACAGGCCCCATTGAACAGCTTCCAGATTATAACCGGATCCGTAGTGGCATGTTCTG
```

FIG. 3C

```
GCTGCGCTTCTAGGCAGGAAGCCTGTGCAGGCGAGGGCGGGGCCGGGGTTCGAGGTTCCCCCCCCACAAACACAC
CACCTCGGTCCTTCAGACCTGTGCAGCTGCTGACTCACCAACCAATAAAGTCTTGCATCGAGAACTGCGTTGTCC
CTCTCTCGTCCTTGGCGTGGAGTCCCCGGGCCATGGTGGGGGAGCAGGGACTTCCCTCGGGTCTGCGTGTCCTGG
ACGCTCTGCCTTCCCACAGGCTGATGTGTCCTTAGTCAGGGGCGAGCGTGGGGGGCTGTAGCCTGGAGGCCGGAA
GCCTTTGATGCCTGCGGGGAGCTGAGGCCAGCTGTTTGCAGTTAGCCACATGGGGGATGCTCCTCACCAGCCTGT
CCTAGGAGAGGGGTGTGGGGGACCATGGGAACTGCAGACCCAGCCTTTACCCTGCTAGGGCTCCCAGCCTAGGGA
TTGAGGTGGGAAGCCCCTTGCTGTGGGTCCTGGGGGTCACCCTCTGGGGGACCCTGGACCCCCCAGACCAGGAG
AGCCCAAGAAATGTCCTCGAGGAAGCCGCCTCTGTGTGTTTACTCTGGATTCTGGGAGGAGGATAGCCCGAGGCA
TAGTGTTCCCATTTGGCTTCTCACTGCTGCCTGGACAGGCAAGGCAAGAATCCTTTGCCTCGATTTGCCGCTGAC
TCAGGCTCTAAGAATATCCCTGAGCTCAGTGGGGCCTGAGCCCCCTCCCTCGACGCGCTCTGTCCCAGGCAAGTC
CTGAGCTGCTGGCCTGGCAGTCCCCTCCCCGTCTGCTGAGGACCTGCTGGAGCTCACAGCTGTCTAGTCCCCTTG
CCACCTCTGGGCTCCGGTCCCCAAGGCAGGAGGGCAGATAGGCCCTCTTCCTGTCCCCCCACCCTTCCAGTCAGG
GTTCCTGGGAGCCCACTGTGGGGTGGATGGAAGTGTGGGCCAGTTTGCCTGTGAGGGAGGTGGTGCTGCCAGTGG
TGGACAGGGTTCTGGGACGAAGTCTGCTGAGAAGGCGGCTATTCAGAAGTGTCCAGAGCACCCACAGTTCACTCC
CACCGCCCCGGTTTCCTCTCCCTTACCCTGTGTGTTGCCATGGCTGCCTGCTGTCCCACGTTTGAGCCCCGGGAG
GATGGGCCTTGGTTTGTCTGCTAAGCCCAGGCCTGGTCCTCAAAGGCCACAGGTGCGCTGGACACAGCAGGCAAG
CTCCCTAGGGTGACGTGGTCCTAGTGGGCCTTGCAGACCTAGCCAGGGAGTTTGATCTCTCCTCCGGAGCCGTAC
TGAGGGAGATGTATTGAGGGTTACTGGGAAGAGGAGTGACTTGCTCAGCTGACAGCCTGGGGACTCAGGAGCATT
TCAGTGTGGTCCCGGTGAGCCAGCACTGTGGCAGCTCTAGTAAGAAAGGGCCTGGGCTGTGGGGGGCACAGGCTA
GACAGCATCCCCAGCAGGGCTGGGGTACCACAGAGGACGGGTGGGTTGGAGGAAGATGACCTGCCCAGCTTTGGC
TGCCGTTCTGAGGAATTTGGAAGTGTCTTAAGACAGTGGGATGTGTGGGGTGAAACCCCCCAAAAGAGGCCCCAG
ATGGAGACATACGGTGCAGAGACTGAAGTAGAGAAGGAAATGTCCAGGGGAGTGTAGGAGGGAGAAAAAGACCTC
TAGGGCCCCACTGCCCAGATGGAGGGAGCTGGTTTCTGGGGCTGGGCCCTAGGCTGTGTGCCTGCCAGGAGGCTG
GAGCCAGGGGCCTCAGAGGGCCACACCCCTGCTCGTGAGCTTCCCGGGAGCACCAGACAGGCACGCGTCTGCAAC
CTACCTTCCACCAACAACCTCTCCTCCCAGCCTTTGAGTGACCCCCTCACAGCAGGCTGCCCTTCCTTTTGGGG
GGTCACTCATGGTTCTGATAAGATGGACACCTGTTCACCTGTTCCTCCAATCTCCCCTAAAGGCCAGACCCAAAT
GTGTGTGTGTCTACACTGTGTACCAGCCCTGCTCTGCACAGCCACCCTTCCGTGCGAGAAGGGGTAAGGGTCTTG
AGGCGGGGCTGCCTCTGTAATGAGAGCCTGTCTGGTTCTCTGCAGCCCTCACCTATAGGACCTATGGGACGGAGG
ACTTGGTGATCCTTGGATGTGGCTGAGAAGATCTTCACCTTGGGAAAAGGTTCTGCGCCCTACGGGTC
```

ASSOCIATION OF *UQCRC1* SNPS WITH FAT DEPOSITION AND FATTY ACID COMPOSITION

INCORPORATION BY REFERENCE

This application claims benefit of U.S. provisional patent application Ser. No. 60/939,715 filed May 23, 2007.

The foregoing applications, and all documents cited therein or during their prosecution ("appln cited documents") and all documents cited or referenced in the appln cited documents, and all documents cited or referenced herein ("herein cited documents"), together with any manufacturer's instructions, descriptions, product specifications, and product sheets for any products mentioned herein or in any document incorporated by reference herein, are hereby incorporated herein by reference, and may be employed in the practice of the invention.

FEDERAL FUNDING LEGEND

This invention was supported, in part, using federal funds from the National Institutes of Health. Accordingly, the Federal Government may have certain rights in this invention.

FIELD OF THE INVENTION

The present invention relates to methods and systems relating to identification of single nucleotide polymorphisms (SNPs) and haplotypes associated with fat deposition and fatty acid composition. The invention further relates to methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Both obesity and type 2 diabetes mellitus (T2DM) are global public health problems and their prevalence will increase dramatically over the coming decades. The rise in obesity has been matched by a rise in diabetes in all ethnic groups in the United States (Caterson et al. Circulation. 2004; 110:e476-483). The Third National Health and Nutrition Examination Survey (National Task Force on the Prevention and Treatment of Obesity. Overweight, obesity, and health risk, Arch Intern Med. 2000; 160:898-904) found that approximately two thirds of adult men and women in the United States diagnosed with type 2 diabetes have a body mass index of 27 or greater. It has been well known that a core characteristic of patients with obesity and T2DM is an increase in insulin resistance, while many studies have indicated that intramyocellular accumulation of triglycerides is a major contributor to insulin resistance (Goodpaster & Wolf, Pediatr Diabetes. 2004; 5:219-226). Interestingly, mitochondrial dysfunction may predispose an individual to intramyocellular lipid accumulation. However, due to the limited protein coding capacity of mitochondria, the initiation and regulation of mitochondrial biogenesis rely heavily on ~1000 nucleus encoded mitochondrial regulatory proteins (Di-Mauro, Mitochondrion. 2004; 4:799-807). The majority of mitochondrial proteins are nuclear encoded, synthesized in the cytosol, and are post-translationally imported into mitochondria. Therefore, most inherited mitochondrial diseases are reported due to mutations in nucleus-encoded mitochondrial genes.

Among a large number of reactions occurring in mitochondria, probably the most impressive of these is oxidative phosphorylation, in which five multi-subunit complexes cooperate to generate most of the cell's energy. Among them, the ubiquinol-cytochrome c reductase complex or complex III is an oligomeric enzyme that catalyzes transfer of electrons from coenzyme QH2 to ferricytochrome c with the coupled translocation of protons across the mitochondrial inner membrane (Brandt & Trumpower, Crit Rev Biochem Mol Biol. 1994; 29:165-197). The bovine heart mitochondrial complex III has been well characterized, which is composed of 11 subunits, including 10 nuclear-encoded subunits and 1 mitochondrial-encoded subunit (Iwata et al. Science. 1998; 281: 64-71).

There is a need for methods that allow relatively easy and more efficient selection and breeding of farm animals that have an advantageous fat deposition and fatty acid composition. The economic significance of the use of genetic markers that are associated with specific economically important traits (especially carcasses and meat quality traits that are hard to measure) in livestock through marker-assisted selection cannot therefore be overemphasized.

Citation or identification of any document in this application is not an admission that such document is available as prior art to the present invention.

SUMMARY OF THE INVENTION

Obesity and type 2 diabetes mellitus (T2DM) constitute leading public health problems worldwide. Studies have shown that insulin resistance affiliated with these conditions is associated with skeletal muscle lipid accumulation, while the latter is associated with mitochondrial dysfunctions. However, the initiation and regulation of mitochondrial biogenesis rely heavily on ~1000 nucleus encoded mitochondrial regulatory proteins.

In the present invention, the ubiquinol-cytochrome c reductase core protein I (UQCRC1) gene, a nuclear-encoded component of mitochondrial complex III, was targeted for its association with fat deposition and fatty acid composition using cattle as a model. Four promoter polymorphisms were identified and genotyped on ~250 Wagyu×Limousin $F_2$ progeny.

Statistical analysis revealed that two completely linked polymorphic sites g.13487C>T and g.13709G>C ($r^2=1$) were significantly associated with both subcutaneous fat depth (SFD) (P<0.01) and skeletal muscle lipid accumulation (SMLA) (P<0.0001). The difference between TTCC and CCGG haplotypes was 0.070 inches for SFD and 0.624 scores for SMLA. Interestingly, the former haplotype produced higher promoter activities than the latter one by 43%-49% in three cell lines (P<0.05). These two SNPs (g.13487C>T and g.13709G>C) also had significant impacts on the estimated stearoyl-CoA desaturase activities designated as $R_2=(16:1/16:0)\times100\%$ and $R_3=(18:1/18:0)\times100\%$ and relative amounts of saturated (SFA), monounsaturated (MUFA) and polyunsaturated fatty acids (PUFA). The polymorphic site g.13671T>C had significant effects on R3 and percent kidney, pelvic and heart fat (KPH), while g.13725G>A was significantly associated with R3 and ribeye area (REA, in $in^2$), respectively. In addition to Rett syndrome and breast/ovarian cancer observed in other studies, overexpression of UQCRC1 might affect mitochondrial morphology and/or physiology and lead to development of obesity and related conditions.

The invention encompasses a method for sub-grouping animals according to genotype wherein the animals of each sub-group have similar polymorphisms in the UQCRC1 gene that may comprise determining the genotype of each animal to be sub-grouped by determining the presence of single nucleotide polymorphisms in the UQCRC1 gene, and segregating individual animals into sub-groups wherein each animal in a sub-group has similar polymorphisms in the UQCRC1 gene.

The invention also encompasses a method for sub-grouping animals according to genotype wherein the animals of each sub-group have a similar genotype in the UQCRC1 gene that may comprise determining the genotype of each animal to be sub-grouped by determining the presence of single nucleotide polymorphism(s) of interest in the UQCRC1 gene, and segregating individual animals into sub-groups depending on whether the animals have, or do not have, the single nucleotide polymorphism(s) of interest in the UQCRC1 gene. The single nucleotide polymorphism(s) of interest may be selected from the group consisting of the follow: four SNPs in the promoter of the UQCRC1 gene:

AAFC03053028.1:g.13487C>T, g.13671T>C, g.13709G>C and g.13725A>G.

The invention further relates to a method for sub-grouping animals according to genotype wherein the animals of each sub-group have similar haplotypes in the UQCRC1 gene that may comprise determining the genotype of each animal to be sub-grouped by determining the presence of any of the above SNPs, and segregating individual animals into sub-groups depending on whether the animals have, or do not have, any of the above SNPs in the UQCRC1 gene.

The invention also relates to method for identifying an animal having a desirable phenotype as compared to the general population of animals of that species, which may comprise determining the presence of single nucleotide polymorphisms in the UQCRC1 gene of the animal, wherein the presence of the SNP's are indicative of a desirable phenotype.

In an advantageous embodiment, the animal may be a bovine. In another advantageous embodiment, the UQCRC1 gene may be a bovine UQCRC1 gene. The invention also encompasses computer-assisted methods and systems for improving the production efficiency for livestock having marketable beef marbling score (BMS) and subcutaneous fat depth (SFD), estimated stearoyl-CoA desaturase activities designated as $R_1=(14:1/14:0)\times100\%$, $R_2=(16:1/16:0)\times100\%$ and $R_3=(18:1/18:0)\times100\%$, relative amounts of saturated (SFA), monounsaturated (MUFA) and polyunsaturated fatty acids (PUFA), conjugated linoleic acid mg/100 g dry muscle (CLA), cholesterol mg/100 g dry muscle (CHOL), ribeye area (REA, in in$^2$) and percent kidney, pelvic and heart fat (KPH), and in particular the genotype of the animals as it relates to UQCRC1 SNPs. Methods of the invention encompass obtaining a genetic sample from each animal in a herd of livestock, determining the genotype of each animal with respect to specific quality traits as defined by a panel of at least two single polynucleotide polymorphisms (SNPs), grouping animals with like genotypes, and optionally, further sub-grouping animals based on like phenotypes and haplotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within the UQCRC1 gene related to feed intake and feed efficiency and associating those data with other data about the animal or its herd, and maintaining those data in ways that are accessible. Another aspect of the invention encompasses a computer-assisted method for predicting which livestock animals possess a biological difference in beef marbling score (BMS) and subcutaneous fat depth (SFD), estimated stearoyl-CoA desaturase activities designated as $R_1=(14:1/14:0)\times100\%$, $R_2=(16:1/16:0)\times100\%$ and $R_3=(18:1/18:0)\times100\%$, relative amounts of saturated (SFA), monounsaturated (MUFA) and polyunsaturated fatty acids (PUFA), conjugated linoleic acid mg/100 g dry muscle (CLA), cholesterol mg/100 g dry muscle (CHOL), ribeye area (REA, in in$^2$) and percent kidney, pelvic and heart fat (KPH), and which may include the steps of using a computer system, e.g., a programmed computer comprising a processor, a data storage system, an input device and an output device, the steps of: (a) inputting into the programmed computer through the input device data that includes a genotype of an animal as it relates to any one of the UQCRC1 SNPs described herein, (b) correlating feed intake and feed efficiency predicted by the UQCRC1 genotypes using the processor and the data storage system and (c) outputting to the output device the feed intake and feed efficiency correlated to the UQCRC1 genotypes, thereby predicting which livestock animals possess improved beef marbling score (BMS) and subcutaneous fat depth (SFD), estimated stearoyl-CoA desaturase activities designated as $R_1=(14:1/14:0)\times100\%$, $R_2=(16:1/16:0)\times100\%$ and $R_3=(18:1/18:0)\times100\%$, relative amounts of saturated (SFA), monounsaturated (MUFA) and polyunsaturated fatty acids (PUFA), conjugated linoleic acid mg/100 g dry muscle (CLA), cholesterol mg/100 g dry muscle (CHOL), ribeye area (REA, in in$^2$) and percent kidney, pelvic and heart fat (KPH).

Yet another aspect of the invention relates to a method of doing business for managing livestock comprising providing to a user a computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein such physical characteristics as feed intake, feed efficiencies, and growth genotypes are associated with the UQCRC1 genotype and haplotypes.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of examples, but not intended to limit the invention solely to the specific embodiments described, may best be understood in conjunction with the accompanying drawings, in which:

FIGS. 3A-3D depict a genomic DNA sequence of the bovine UQCRC1 gene (edited from AAFC03053028.1). The cDNA sequence is shaded, SNPs are bolded, shaded and underlined and primer sequences are underlined.

DETAILED DESCRIPTION

Figure 1A:
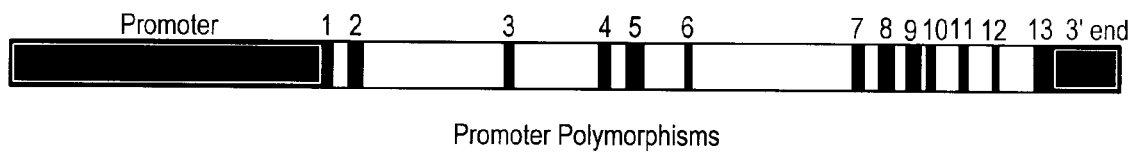
FIGS. 1A-1B depict a genomic organization (A) and haplotype analysis (B) in the bovine UQCRC1 gene. Pairwise linkage disequilibrium relationship for 4 mutations is illustrated based on $r^2$ measurements.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol I and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UITma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 370 Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene(s) of interest is a bovine UQCRC1 gene, the bovine UQCRC1 nucleotide sequences can be selected from, but is not limited to, GenBank Accession No. AAFC03053028.1. The gene(s) of interest include, but are not limited to, the sequences corresponding to four SNPs in the promoter of the UQCRC1 gene: AAFC03053028.1:g.13487C>T, g.13671T>C, g.13709G>C and g.13725A>G, respectively, or fragments thereof or a region of the bovine genome that comprises said sequence(s).

The present invention, therefore, provides isolated nucleic acids that may specifically hybridize to the nucleotide sequence corresponding to four SNPs in the promoter AAFC03053028.1:g.13487C>T, g.13671T>C, g.13709G>C and g.13725A>G.

The single nucleotide polymorphism(s) of interest may be selected from the group comprising the nucleotide substitutions defined in four SNPs in the promoter AAFC03053028.1:g.13487C>T, g.13671 T>C, g.13709G>C and g.13725A>G.

The SNPs advantageous in the present invention are associated with certain economically valuable and heritable traits relating to meat quality in bovines. Therefore, it is an object of the present invention to determine the genotype of a given animal of interest as defined by the nucleotide substitutions selecting from the group consisting of four SNPs in the promoter AAFC03053028.1:g.13487C>T, g.13671T>C, g.13709G>C and g.13725A>G, according to the present invention. It is also contemplated that the genotype of the animal(s) may be defined by additional SNPs within the UQCRC1 gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits to be identified based on the presence of SNPs in their genomes and particularly with SNPs located within the UQCRC1 gene. The methods further allow, by computer-assisted methods of the invention, to correlate SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the UQCRC1 gene, advantageously of the region encompassing an UQCRC1 SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with an UQCRC1 gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in an UQCRC1 gene which are unique to an UQCRC1 gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi &

Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3$H, $^{125}$I, $^{35}$S, $^{14}$C, $^{32}$P, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mis-matched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g. horseradish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and MacBeath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved meat quality and yield, in particular meat tenderness. Continuous selection and breeding of animals, such as livestock, that are at least heterozygous and advantageously homozygous for desirable alleles of the UQCRC1 gene polymorphic sites associated with subcutaneous fat depth (SFD), skeletal muscle lipid accumulation (SMLA), estimated stearoyl-CoA desaturase activities designated as R2=(16:1/16:0)×100% and R3=(18:1/18:0)×100%, relative amounts of saturated (SFA), monounsaturated (MUFA) and polyunsaturated fatty acids (PUFA), ribeye area (REA, in in2) and percent kidney, pelvic and heart fat (KPH). Thus, the UQCRC1 SNPs of the present invention can be used as a selection tool.

Desirable phenotypes may also include, but are not limited to, feed intake, growth rate, body weight, carcass merit and composition, and milk yield. Specific carcass traits with desirable phenotypes include, but are not limited to, additional carcass value (additional carc value, $), average daily gain (ADG, lb/d), backfat thickness (BFAT, in), beef marbling score (BMS), calculated live weight (Calc Lv Wt, lb), calculated yield grade (cYG), cholesterol mg/100 g dry muscle (CHOL), conjugated linoleic acid mg/100 g dry muscle (CLA), days on feed (DOF, d), dressing percentage (DP, %), dry matter intake (DMI, lb), dry matter intake per day on feed (DMI per DOF, lb/d), estimated stearoyl-CoA desaturase activities, hot carcass weight (HCW, lb), hot carcass weight value (HCW value, $), intramuscular fat content (IMF %, %), marbling score (MBS, 10 to 99), marbling score divided by days on feed (MBS/DOF), percent kidney, pelvic and heart fat (KPH), quality grade, less than or equal to select versus greater than or equal to choice (QG, <Se vs, >Ch), relative amounts of saturated (SFA), monounsaturated (MUFA) and polyunsaturated fatty acids (PUFA), ribeye area (REA, in2), ribeye area per hundred weight HCW (REA/cwt HCW, in2/100 lb hot carcass weight (HCW) subcutaneous fat depth (SFD).

One aspect of the present invention provides for grouping animals and methods for managing livestock production comprising grouping livestock animals such as cattle according the genotype as defined by panels of SNPs, each panel comprising at least one SNP, one or more of which are in the UQCRC1 gene of the present invention. Other SNPs that may be included in panels of SNPs include, but not limited to, SNPs found in the calpastatin gene, CRH gene, FGF8 gene, GHR gene, TFAM gene, GHR gene, FABP4 gene, ghrelin gene, leptin gene, NPY gene, ob gene, UASMS1 gene, UASMS2 gene, UASMS3 gene, UCN gene, UCP2 gene, UTS2 gene and/or UTS2R gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, feed intake, carcass/meat quality and milk production. The present invention provides methods of screening livestock to determine those more likely to develop a desired body condition by identifying the presence or absence of one or more gene polymorphisms correlated with meat quality.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by SNP genotype. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or subgrouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin, MMI (Meta Morphix Inc.), bovine spongiform encephalopathy (BSE) diagnosis, brucellosis vaccination, FMD (foot and mouth disease) vaccination, BVD (bovine viral diarrhea) vaccination, Sure Health preconditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are UQCRC1 sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the UQCRC1 sequences described herein.

Another embodiment of the invention is an oligonucleotide that specifically hybridizes under high stringency conditions to any one of the polymorphic sites of the UQCRC1 gene, wherein the oligonucleotide is between about 18 nucleotides and about 50 nucleotides.

In another embodiment of the invention, the oligonucleotide comprises a central nucleotide specifically hybridizing with a UQCRC1 gene polymorphic site of the portion of the nucleic acid molecule.

Another aspect of the invention is a method of identifying a UQCRC1 polymorphism in a nucleic acid sample comprising isolating a nucleic acid molecule encoding UQCRC1 gene or a fragment thereof and determining the nucleotide at the polymorphic site.

Another aspect of the invention is a method of screening cattle to determine those bovines more likely to exhibit a biological difference in meat quality comprising the steps of obtaining a sample of genetic material from a bovine; and assaying for the presence of a genotype in the bovine which is associated with meat quality, the genotype characterized by polymorphisms in the UQCRC1 gene.

In other embodiments of this aspect of the invention, the step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the UQCRC1 gene or a portion thereof that contains the polymorphism. In other embodiments of the invention, the amplification may include the step of selecting a forward and a reverse sequence primer capable of amplifying a region of the UQCRC1 gene.

Another aspect of the invention is a computer-assisted method for predicting which livestock animals possess a biological difference in meat quality comprising: using a computer system, e.g., a programmed computer comprising a processor, a data storage system, an input device and an output device, the steps of: (a) inputting into the programmed computer through the input device data comprising an UQCRC1 genotype of an animal, (b) correlating growth, feed intake, efficiency or carcass merit quality predicted by the UQCRC1 genotype using the processor and the data storage system and (c) outputting to the output device the meat quality correlated to the UQCRC1 genotype, thereby predicting which livestock animals possess a particular growth level, feed intake, efficiency or carcass merit quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

Highly Expressed UQCRC1 Promoter SNPs Increase Subcutaneous and Muscle Lipid Accumulation Both obesity and type 2 diabetes mellitus (T2DM) are global public health problems and their prevalence will increase dramatically over the coming decades. The rise in obesity has been matched by a rise in diabetes in all ethnic groups in the United States (1). The Third National Health and Nutrition Examination Survey (2) found that approximately two thirds of adult men and women in the United States diagnosed with type 2 diabetes have a body mass index of 27 or greater. It has been well known that a core characteristic of patients with obesity and T2DM is an increase in insulin resistance, while many studies have indicated that intramyocellular accumulation of triglycerides is a major contributor to insulin resistance (3). Interestingly, mitochondrial dysfunction may predispose an individual to intramyocellular lipid accumulation. However, due to the limited protein coding capacity of mitochondria, the initiation and regulation of mitochondrial biogenesis rely heavily on ~1000 nucleus encoded mitochondrial regulatory proteins (4). The majority of mitochondrial proteins are nuclear encoded, synthesized in the cytosol, and are post-translationally imported into mitochondria. Therefore, most inherited mitochondrial diseases are reported due to mutations in nucleus-encoded mitochondrial genes.

Among a large number of reactions occurring in mitochondria, probably the most impressive of these is oxidative phosphorylation, in which five multi-subunit complexes cooperate to generate most of the cell's energy. Among them, the ubiquinol-cytochrome c reductase complex or complex III is an oligomeric enzyme that catalyzes transfer of electrons from coenzyme QH2 to ferricytochrome c with the coupled translocation of protons across the mitochondrial inner membrane (5). The bovine heart mitochondrial complex III has been well characterized, which is composed of II subunits, including 10 nuclear-encoded subunits and 1 mitochondrial-encoded subunit (6). In the present Example, genomic organization of the bovine ubiquinol-cytochrome c reductase core protein I (UQCRC1), a nuclear-encoded component, was determined and four genetic markers in its promoter region were developed. Statistical analysis using general linear model (GLM) and quantitative transmission-disequilibrium test (QTDT) revealed that promoter polymorphisms are significantly associated with both SFD and SMLA in Wagyu×Limousin $F_2$ cross cattle. The result provides evidence that some cases of obesity and T2DM might be classified into the mitochondria-related diseases.

Obesity and type 2 diabetes mellitus (T2DM) constitute leading public health problems worldwide. Studies have shown that insulin resistance affiliated with these conditions is associated with skeletal muscle lipid accumulation, while the latter is associated with mitochondrial dysfunctions. However, the initiation and regulation of mitochondrial biogenesis rely heavily on ~1000 nucleus encoded mitochondrial regulatory proteins. In the present Example, the ubiquinol-cytochrome c reductase core protein I (UQCRC1) gene, a nuclear-encoded component of mitochondrial complex III, was targeted for its association with subcutaneous fat depth (SFD) and skeletal muscle lipid accumulation (SMLA) using cattle as a model. Four promoter polymorphisms were identified and genotyped on ~250 Wagyu x Limousin $F_2$ progeny. Statistical analysis revealed that two completely linked polymorphic sites g.13487C>T and g.13709G>C ($r^2$=1) were significantly associated with both SFD (P<0.01) and SMLA (P<0.0001). The difference between TTCC and CCGG haplotypes was 0.070 inches for SFD and 0.624 scores for SMLA. Interestingly, the former haplotype produced higher promoter activities than the latter one by 43%-49% in three cell lines (P<0.05). In addition to Rett syndrome and breast/ovarian cancer observed in other studies, that overexpression of UQCRC1 might affect mitochondrial morphology and/or physiology and lead to development of obesity and related conditions.

The cDNA sequence of the bovine UQCRC1 gene was cloned many years ago (7). Alignment between the cDNA (NM_174629) and its genomic DNA contig (AAFC03053028) retrieved from the bovine whole genome shotgun sequence indicated that like its human ortholog, the bovine gene consists of 13 exons (FIG. 1A). Screening of genetic polymorphisms on six Wagyu×Limousin $F_1$ bulls detected four SNPs in the promoter region: AAFC03053028.1:g.13487C>T, g.13671T>C, g.13709G>C and g.13725A>G, respectively. The minor alleles among these four SNPs are T, T, C and A, respectively, with a frequency ranging from 0.079 to 0.299 (Table 1). Sequencing on ~250 F2 progeny indicated that all four SNPs fall into Hardy-Weinberg equilibrium (P>0.05) (Table 1).

TABLE 1

Hardy-Weinberg equilibrium (HWE) test of four SNPs in the promoter region of bovine UQCRC1 gene

| | | | | | LOD | | |
|---|---|---|---|---|---|---|---|
| SNP | HWE | Minor allele | Frequency | C > T | T > C | G > C | A > G |
| 13487C > T | 0.42 | T | 0.299 | — | 15.81 | 101.10 | 2.71 |
| 13671T > C | 0.12 | T | 0.297 | | — | 15.81 | 0.15 |
| 13709G > C | 0.42 | C | 0.299 | | | — | 2.71 |
| 13725A > G | 0.39 | A | 0.079 | | | | — |

Figure 1B:
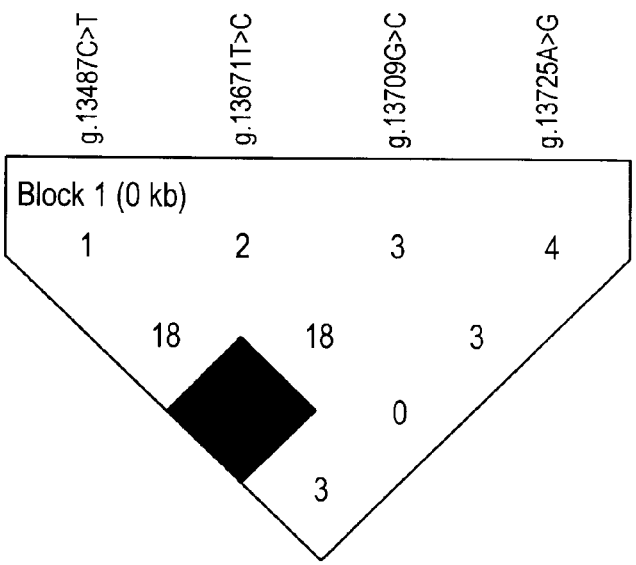

Initial sequencing of the promoter region on six Wagyu× Limousin $F_1$ bulls indicated that both g.13487C>T and g.13709G>C form two haplotypes: CG and TC. The HAPLOVIEW analysis on genotype data of all $F_2$ progeny further confirmed the no-historical recombination status between these two SNPs with a $r^2$ value of 1 (FIG. 1B). Two markers, AAFC03053028.1:g.13671T>C and g.13725A>G are still segregating in the population. In particular, the linkage was hardly detected between g.13725A>G and three other SNPs because of logarithm of the odds (LOD) scores of <3.0 (Table 1). A total of four haplotypes among these four SNPs were identified in the population using the HAPLOVIEW program, including CCGG, TCCG, CTGG and CCGA with a frequency of 0.325, 0.299, 0.297 and 0.079, respectively.

As both SNPs g.13487C>T and g.13709G>C have no-historical recombination events in the population, three tagging SNPs—g.13487C>T, g.13671T>C, g.13725A>G were used in the association analysis. Overall, the F2 population had an average SFD of 0.394 inches with a standard deviation of 0.18 inches. Both GLM analysis and QTDT test revealed that only SNP g.13487C>T was significantly associated with SFD in the population (P=0.0040 for GLM analysis, and P=0.0022 for QTDT test, respectively) (Table 2). The CC animals had 0.070 inches of SFD less than the TT animals and 0.067 less than the CT heterozygotes. Both TT and CT animals contained equal amounts of SFD, indicating that the T allele is almost completely dominant to the C allele (Table 2).

TABLE 2

Associations of UQCRC1 promoter polymorphisms with SFD and SMLA in a Wagyu x Limousin reference population

| | | | | GLM analysis | | QTDT test | |
|---|---|---|---|---|---|---|---|
| SNP | Genotype | N | LSM ± S.E. | F value | P | $\chi^2$ | P |
| Subcutaneous fat depth (SFD) in inches | | | | | | | |
| 13487C > T | CC | 121 | $0.364 \pm 0.014^a$ | 5.66 | 0.0040 | 9.34 | 0.0022 |
| | CT | 95 | $0.431 \pm 0.016^b$ | | | | |
| | TT | 25 | $0.434 \pm 0.031^b$ | | | | |
| 13671T > C | TT | 16 | $0.382 \pm 0.039^a$ | 1.81 | 0.1667 | 2.96 | 0.0855 |
| | CT | 112 | $0.379 \pm 0.015^a$ | | | | |
| | CC | 113 | $0.418 \pm 0.015^a$ | | | | |
| 13725A > G | GG | 205 | $0.393 \pm 0.011^a$ | 0.68 | 0.5082 | 1.29 | 0.2566 |
| | AG | 36 | $0.427 \pm 0.027^a$ | | | | |
| Skeletal muscle lipid accumulation (SMLA) in marbling scores | | | | | | | |
| 13487C > T | CC | 121 | $5.638 \pm 0.088^a$ | 10.69 | <0.0001 | 17.76 | <0.0001 |
| | CT | 95 | $6.197 \pm 0.099^b$ | | | | |
| | TT | 25 | $6.262 \pm 0.193^b$ | | | | |

TABLE 2-continued

Associations of UQCRC1 promoter polymorphisms with SFD and SMLA in a Wagyu × Limousin reference population

| SNP | Genotype | N | LSM ± S.E. | GLM analysis | | QTDT test | |
|---|---|---|---|---|---|---|---|
| | | | | F value | P | $\chi^2$ | P |
| 13671T > C | TT | 16 | 5.631 ± 0.249$^a$ | 2.27 | 0.1058 | 4.54 | 0.0332 |
| | CT | 112 | 5.827 ± 0.094$^a$ | | | | |
| | CC | 113 | 6.059 ± 0.093$^a$ | | | | |
| 13725A > G | GG | 205 | 5.903 ± 0.069$^a$ | 1.41 | 0.2426 | 0.56 | 0.4544 |
| | AG | 36 | 6.080 ± 0.169$^a$ | | | | |

Overall, all $F_2$ progeny had an average marbling score of 5.916, which is a subjective, visual appraisal of the fat on a meat cut surface. The polymorphic site g.13487C>T showed an extremely significant association with the trait (P<0.0001 for both GLM and QTDT tests) (Table 2). Animals with the CC genotypes had marbling scores that were 0.624 and 0.559 lower than animals with TT and CT genotypes, respectively. Again, allele T is dominant to allele C, but by increasing the fat deposition in muscle. Interestingly, GLM analysis indicated marker 13671T>C approaching the significance, but QTDT test further confirmed that this SNP was also significantly associated with SMLA (Table 2). The difference in marbling scores was 0.428 between TT and CC homozygotes, which also approaches the significance level (P=0.0813). No significant association was observed between g.13725A>G and SMLA in the population (Table 2). In humans, the fat stored in muscle is classified into intramyocellular (IMCL) and extramyocelluar (EMCL) lipid content. By definition, the muscle lipid accumulation measured by marbling score in the present study would mostly represent the EMCL content, because the IMCL can not be observed by eyes. However, most methods for quantifying IMCL content, such as computed tomography, magnetic resonance imaging, magnetic resonance spectroscopy and biochemical analysis can not truly separate IMCL and EMCL (8). Furthermore, both IMCL and EMCL contents in human subjects are highly correlated with each other (r=0.68) (9). As well, both measurements are also highly correlated with % total body fat (r=0.69 for IMCL and r=0.66 for EMCL), body mass index (r=0.67 for IMCL and r=0.68 for EMCL), visceral fat (r=0.73 for IMCL and r=0.86 for EMCL) and insulin-to-glucose ratio (r=0.72 for IMCL and r=0.68 for EMCL), respectively [9]. These data provide evidence that both IMCL and EMCL might equally contribute to development of T2DM and obesity in humans.

Figure 2A:
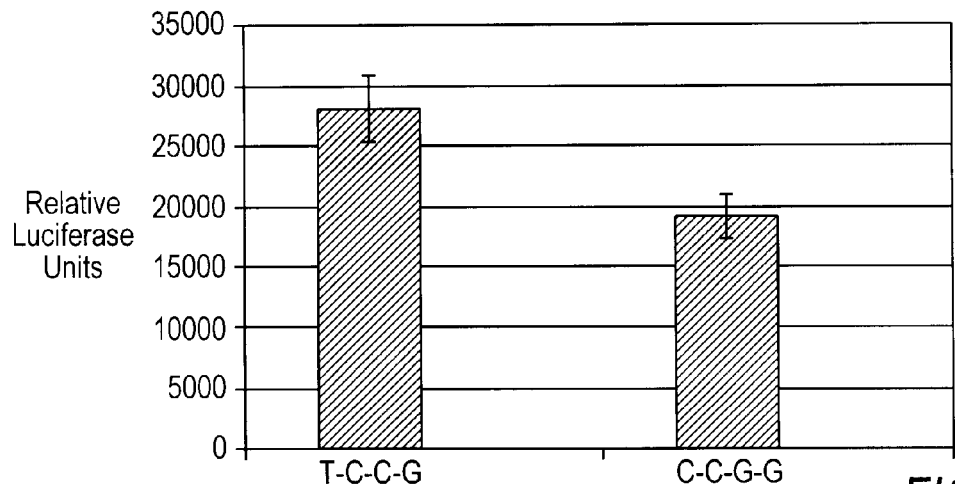
FIGS. 2A-2C depict effects of haplotypes on promoter activity in the H1299 cells (A), HCT116 cells (B) and Cos7 cells (C).
Figure 2B:
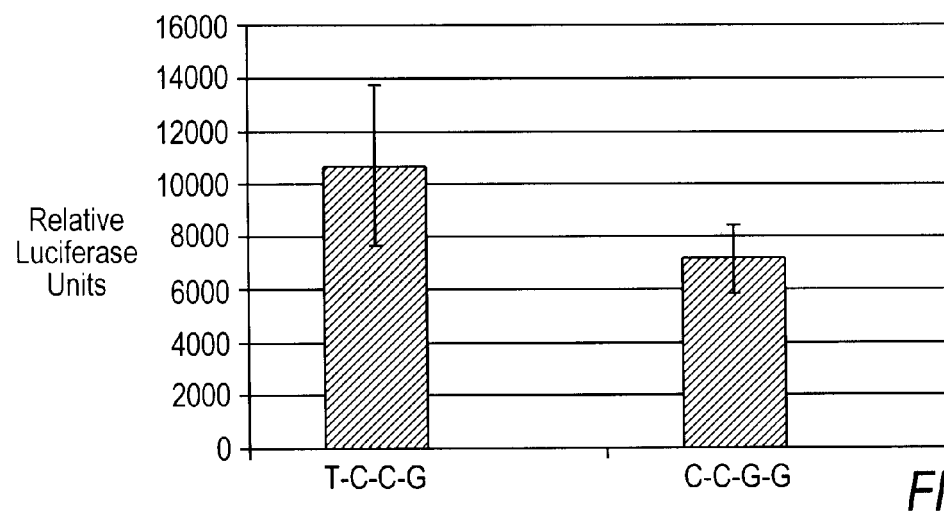
Figure 2C:
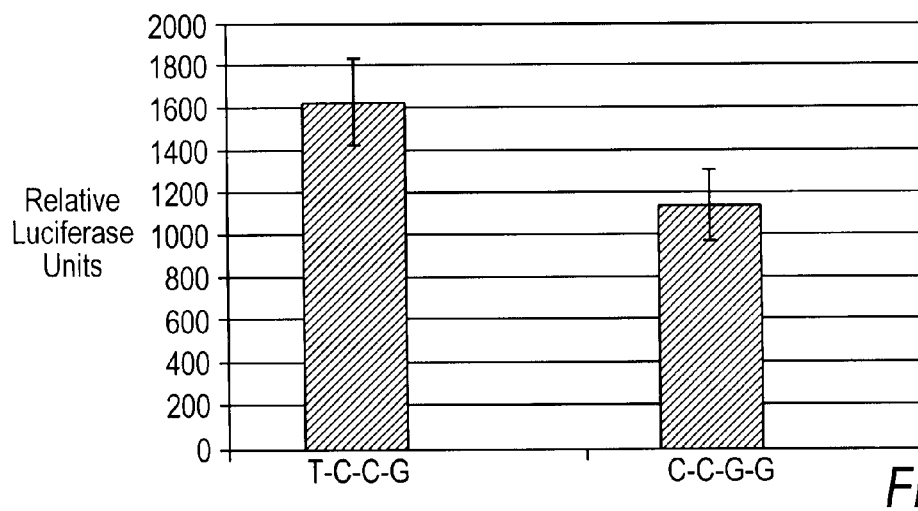

As indicated above, the polymorphic site g.13487C>T was significantly associated with both SFD and SMLA in the population (Table 2) and it had no-historical recombination with g.13709G>C (FIG. 1B). Therefore, only two haplotype constructs: T-C-C-G and C-C-G-G that are different at both g.13487C>T and g.13709G>C sites, but the same at g.13671T>C and g.13725A>G sites, were used to investigate how these associated mutations affect promoter activities of the bovine UQCRC1 gene in three cell lines. Overall, the former construct produced higher promoter activities than the latter construct by 47% in the H1299 cells (P=0.0073), 49% in the HCT116 cells (P=0.0197) and 43% in the Cos7 cells (P=0.0185), respectively (FIGS. 2A, 2B and 2C). In the H1299 cells, the average firefly luciferase activity was 28,133±2,782 for the T-C-C-G haplotype and 19,146±1,903 for the C-C-G-G haplotype, respectively (FIG. 2A). In the HCT116 cells, the former haplotype resulted in an average of 10,713±3,046 promoter activity, while the latter haplotype yielded an average of 7,183±1,250 promoter activity (FIG. 2B). The Cos7 cells had the lowest promoter activities, but the difference between the two haplotypes was still significant (1,627±208 for the T-C-C-G construct and 1,140±167 for the C-C-G-G construct, respectively) (FIG. 2C).

As indicated above, UQCRC1 encodes a subunit of mitochondrial respiratory complex III, which operates through a Q-cycle mechanism that couples electron transfer to generation of the proton gradient that drives ATP synthesis. Recent studies have demonstrated that overexpression of UQCRC1 might affect mitochondrial morphology and/or physiology and thus cause mitochondrial dysfunction and diseases. In the Mecp2-null mouse, an animal model for Rett syndrome, Kriaucionis and colleagues (10) found that Uqcrc1 was significantly up-regulated in early- and late-symptomatic brains. Uqcrc1 overexpression correlated positively with symptom severity and with a significant increase in mitochondrial respiratory capacity and a reduction in respiratory efficiency. In humans, UQCRC1 was highly expressed in breast (74%) and ovarian tumors (34%) (11). In the present study, it was observed that the haplotype that produced the higher promoter activity was also associated with an increase of both SFD and SMLA in the cattle model. Compared to the C-G haplotype at g.13487C>T and g.13709G>C sites, the T-C haplotype yielded 43% to 49% more promoter activity (FIG. 2). As well, the animals with the T-C haplotype had a marbling score that was 0.624 higher and 0.07 inches more SFD than the animals with the T-C haplotype (Table 2). Therefore, this study for the first time demonstrates the existence of cross talk between the mitochondria and UQCRC1/complex III in the regulation of energy metabolism and balance.

A previous study confirmed a conserved segment of ~12 Mb from CLEC3B (C-type lectin domain family 3, member B) to ERC2 (ELKS/RAB6-interacting/CAST family member 2) between human chromosome 3p22.3-p14.3 and bovine chromosome 22q24 (12). Just recently, Harder and colleagues (13) found this region harbors quantitative trait loci (QTL) for the persistency of fat yield and the persistency of milk energy yield in dairy cattle using 16 paternal half-sib families with a total of 872 bulls. The QTLs surround the lactotransferrin (LTF) gene, while the UQCRC1 is located 2 Mb apart. Therefore, this could be another case to support the involvement of UQCRC1 gene in fat deposition and energy production. In addition to the UQCRC1 gene presented here, two other nucleus encoded mitochondrial genes—mitochondrial transcription factor A (TFAM) and fatty acid binding protein 4 (FABP4) were found to be associated with both beef marbling score and SFD in the same population of cattle (14-15). The current human obesity gene map also displayed 48 genes that are nucleus encoded mitochondrial genes (16). Overall, mutations in nuclear mitochondrial genes have been shown to lead to oxidative stress, neurodegenerative diseases, and metabolic disorders. Therefore, how nucleus encoded mitochondrial genes relate to obesity and its related conditions need to be further addressed by the obesity research community.

Animals. Development of a Wagyu x Limousin reference population was previously described (14). The Japanese Wagyu breed of cattle has been traditionally selected for high muscle lipid accumulation, whereas the Limousin breed has been selected for heavy muscle, which leads to low fat deposition in muscle. The difference in SMLA between these two breeds makes them very unique for mapping quantitative trait loci (QTLs) for obesity-related traits. Beef marbling score was a subjective measure of the amount of fat stored in the longissimus muscle based on USDA standards, definitions and explanations for which can be found, for example, at the USDA Agricultural Marketing Services web pages. Subcutaneous fat depth (SFD) was measured at the 12-13$^{th}$ rib interface perpendicular to the outside surface at a point three-fourths the length of the longissimus muscle from its chine bone end. The marbling scores for SMLA ranged from 4 to 9.5 and SFD varied from 0.1 to 1.3 inches in the population.

Mutation detection and genotyping. A pair of primers (forward, 5'-GAA GGA AGG TAC ACC GGA AGG AAT A-3' and reverse: 5'-TAA GGC AAA TTG TGC ATG GCT GTA-3') was designed to target the promoter region of the bovine UQCRC1 gene (FIG. 3). Approximately 50 ng of genomic DNA each from six WagyuxLimousin $F_1$ bulls was amplified in a final volume of 10 µL that contained 12.5 ng of each primer, 150 µM dNTPs, 1.5 mM MgCl$_2$, 50 mM KCl, 20 mM Tris-HCl and 0.25 U of Platinum Taq polymerase (Invitrogen, Carlsbad, Calif.). The PCR conditions were carried out as follows: 94° C. for 2 min, 35 cycles of 94° C. for 30 sec, 60° C. for 30 sec and 72° C. for 30 sec, followed by a further 5 min extension at 72° C. PCR products were then sequenced on an ABI 3730 sequencer in the Laboratory for Biotechnology and Bioanalysis (Washington State University) using a standard protocol and polymorphisms were identified. The same PCR product direct sequencing approach was also used to genotype the polymorphisms on ~250 $F_2$ progeny.

Data analysis. The degrees of Hardy-Weinberg equilibrium within each marker and linkage disequilibrium plus haplotypes among different markers in the bovine UQCRC1 gene were estimated using the HAPLOVIEW program (17). The phenotypic data for both IMCL and SFD measurements have been previously adjusted for year of birth, sex, age (days), live weight (kilograms), or fat depth (inches), as appropriate. The adjusted phenotypes were then used in a subsequent association analysis using the GLM (general linear model) procedure of SAS v9.1 (SAS institute Inc., Gary, N.C.). Pair-wise comparisons of least squares means were performed using a protected t-test. Additionally, quantitative transmission disequilibrium test (QTDT) (18) was performed to further examine the association between markers and adjusted obesity-related phenotype data. P value<0.05 was considered statistically significant.

Promoter activity assay. The forward and reverse gene-specific primers described above were engineered with a 5' SacI and 3' HindIII site plus a 5' tail of CTTC, respectively, for directional cloning into the SacI/HindIII site of pGL3-basic (Premega, Madison, Wis.). Two types of haplotypes T-C-C-G and C-C-G-G were prepared for the promoter constructs. Human lung carcinoma H1299 cells, colorectal carcinoma HCT116 cells and Simian kidney COS-7 cells were transfected with each of the recombinant pGL3 plasmids containing the constructs described above. pRL-CMV plasmid was also co-transfected into these cell lines as a transfection control. All cells were collected 48 hours post-transfection and firefly luciferase activities were measured with the Dual Luciferase Reporter Assay system according to the manufacturer's protocol. Light emission was quantified with a Multi-label Counter (Wallace 1420 Victor 2, Turku, Finland). Triplicate data were collected and were T-tested for significance.

REFERENCES CITED

1. Caterson I D, Hubbard V, Bray G A et al. Prevention Conference VII: Obesity, a worldwide epidemic related to heart disease and stroke: Group III: worldwide comorbidities of obesity. Circulation. 2004; 110:e476-483.

2. National Task Force on the Prevention and Treatment of Obesity. Overweight, obesity, and health risk, Arch Intern Med. 2000; 160:898-904.

3. Goodpaster B H, Wolf D. Skeletal muscle lipid accumulation in obesity, insulin resistance, and type 2 diabetes. Pediatr Diabetes. 2004; 5:219-226.

4. DiMauro S. The many faces of mitochondrial diseases. Mitochondrion. 2004; 4:799-807.

5. Brandt U, Trumpower B. The protonmotive Q cycle in mitochondria and bacteria. Crit Rev Biochem Mol Biol. 1994; 29:165-197.

6. Iwata S, Lee J W, Okada K et al. Complete structure of the 11-subunit bovine mitochondrial cytochrome bc1 complex. Science. 1998; 281:64-71.

7. Gencic S, Schagger H, von Jagow G. Core I protein of bovine ubiquinol-cytochrome-c reductase; an additional member of the mitochondrial-protein-processing family. Cloning of bovine core I and core II cDNAs and primary structure of the proteins. Eur J. Biochem. 1991; 199:123-131.

8. Schrauwen-Hinderling V B, Hesselink M K, Schrauwen P, Kooi M E. Intramyocellular lipid content in human skeletal muscle. Obesity. 2006; 14:357-367.

9. Sinha R, Dufour S, Petersen K F et al. Assessment of skeletal muscle triglyceride content by (1)H nuclear magnetic resonance spectroscopy in lean and obese adolescents: relationships to insulin sensitivity, total body fat, and central adiposity. Diabetes. 2002; 51:1022-1027.

10. Kriaucionis S, Paterson A, Curtis J, Guy J, Macleod N, Bird A. Gene expression analysis exposes mitochondrial abnormalities in a mouse model of Rett syndrome. Mol Cell Biol. 2006; 26:5033-5042.

11. Kulawiec M, Arnouk H, Desouki M M, Kazim L, Still I, Singh K K. Proteomic analysis of mitochondria-to-nucleus retrograde response in human cancer. Cancer Biol Ther. 2006; 5:967-975.

12. Griffin K B, Michal J J, Fox L K, Gaskins C T, Jiang Z. Fine mapping of the bovine chromosome 22q24 region that harbours antimicrobial genes and a QTL for somatic cell score. Anim Genet. 2005; 36:448-450.

13. Harder B, Bennewitz J, Reinsch N et al. Mapping of quantitative trait loci for lactation persistency traits in German Holstein dairy cattle. J Anim Breed Genet. 2006; 123: 89-96.

14. Jiang Z, Kunej T, Michal J J et al. Significant associations of the mitochondrial transcription factor A promoter polymorphisms with marbling and subcutaneous fat depth in WagyuxLimousin F2 crosses. Biochem Biophys Res Commun. 2005; 334:516-523.

15. Michal J J, Zhang Z W, Gaskins C T, Jiang Z. The bovine fatty acid binding protein 4 gene is significantly associated with marbling and subcutaneous fat depth in Wagyux Limousin F2 crosses. Anim Genet. 2006; 37:400-402.

16. Rankinen T, Zuberi A, Chagnon Y C et al. The human obesity gene map: the 2005 update. Obesity. 2006; 14:529-644.

17. Barrett J C, Fry B, Maller J, Daly M J. Haploview: analysis and visualization of LD and haplotype maps. Bioinformatics. 2005; 21:263-265.

18. Abecasis G R, Cardon L R, Cookson W O. A general test of association for quantitative traits in nuclear families. Am J Hum Genet. 2000; 66:279-292.

Example 2

Single Marker Associations

TABLE 3

Single marker details

| Marker | Genotypes | Counts | Frequency |
|---|---|---|---|
| CRHE2133 | CC | 275 | 0.183 |
| CRHE2133 | CG | 704 | 0.469 |
| CRHE2133 | GG | 523 | 0.348 |
| CRHE2351 | CC | 98 | 0.065 |
| CRHE2351 | CG | 551 | 0.367 |

TABLE 3-continued

Single marker details

| Marker | Genotypes | Counts | Frequency |
|---|---|---|---|
| CRHE2351 | GG | 853 | 0.568 |
| UCN3E2270 | AA | 344 | 0.229 |
| UCN3E2270 | AC | 722 | 0.481 |
| UCN3E2270 | CC | 434 | 0.289 |
| UCN3P232 | CC | 775 | 0.514 |
| UCN3P232 | CT | 606 | 0.402 |
| UCN3P232 | TT | 126 | 0.084 |
| UQCRC1P059 | CC | 879 | 0.586 |
| UQCRC1P059 | CT | 542 | 0.361 |
| UQCRC1P059 | TT | 80 | 0.053 |
| UTS2RP372 | DD | 263 | 0.176 |
| UTS2RP372 | ID | 748 | 0.499 |
| UTS2RP372 | II | 487 | 0.325 |

TABLE 4

Single marker associations

| Marker | Trait | DDFM | Estimate | StdErr | P-Value | Estimate | StdErr | P-Value | ProbF |
|---|---|---|---|---|---|---|---|---|---|
| CRHE2351 | Cuttability | 1439 | 0.310 | 0.065 | 2.37E−06 | 0.237 | 0.165 | 0.1514 | 2.224E−06 |
| CRHE2351 | Yield Grade | 1439 | −0.132 | 0.028 | 2.93E−06 | −0.101 | 0.071 | 0.1568 | 2.771E−06 |
| CRHE2351 | Rib eye area | 1446 | 0.293 | 0.067 | 1.13E−05 | 0.145 | 0.168 | 0.3890 | 3.509E−06 |
| CRHE2351 | Backfat | 1428 | −0.026 | 0.006 | 1.99E−05 | −0.031 | 0.015 | 0.0389 | 8.378E−05 |
| CRHE2351 | Residual Feed Intake | 1428 | 0.202 | 0.061 | 0.0010 | 0.321 | 0.154 | 0.0371 | 0.0043 |
| CRHE2351 | Backfat Rate | 1428 | 0.000 | 0.000 | 0.0044 | −0.001 | 0.000 | 0.0311 | 0.0154 |
| CRHE2351 | Feed conversion ratio | 1446 | 0.039 | 0.018 | 0.0280 | 0.097 | 0.045 | 0.0312 | 0.0542 |
| CRHE2351 | Hot Carcass Weight | 1446 | 5.883 | 2.787 | 0.0350 | 4.564 | 7.015 | 0.5154 | 0.0753 |
| CRHE2351 | Live Weight | 1446 | 8.671 | 4.166 | 0.0376 | 8.624 | 10.483 | 0.4108 | 0.0956 |
| CRHE2351 | Daily feed intake | 1446 | 0.221 | 0.119 | 0.0642 | 0.226 | 0.300 | 0.4514 | 0.1580 |
| CRHE2351 | Percent Choice | 1436 | −0.025 | 0.021 | 0.2201 | 0.012 | 0.052 | 0.8201 | 0.2084 |
| CRHE2351 | Marbling | 1062 | −3.469 | 4.228 | 0.4121 | −4.634 | 10.540 | 0.6603 | 0.7113 |
| CRHE2351 | Average Daily Gain | 1446 | 0.013 | 0.019 | 0.5054 | −0.022 | 0.047 | 0.6459 | 0.4272 |
| CRHE2351 | Dressing Percent | 1446 | 0.046 | 0.083 | 0.5777 | −0.038 | 0.210 | 0.8557 | 0.6805 |
| CRHE2351 | Days on Feed | 1446 | 0.029 | 0.112 | 0.7917 | −0.047 | 0.281 | 0.8683 | 0.8828 |
| CRHE2133 | Rib eye area | 1445 | 0.154 | 0.059 | 0.0096 | 0.064 | 0.108 | 0.5550 | 0.0037 |
| CRHE2133 | Hot Carcass Weight | 1445 | 5.084 | 2.466 | 0.0394 | 4.478 | 4.469 | 0.3165 | 0.0821 |
| CRHE2133 | Feed conversion ratio | 1445 | 0.033 | 0.016 | 0.0398 | 0.041 | 0.029 | 0.1573 | 0.1177 |
| CRHE2133 | Yield Grade | 1438 | −0.048 | 0.025 | 0.0562 | −0.021 | 0.046 | 0.6404 | 0.0510 |
| CRHE2133 | Cuttability | 1438 | 0.111 | 0.059 | 0.0583 | 0.054 | 0.106 | 0.6116 | 0.0594 |
| CRHE2133 | Live Weight | 1445 | 6.928 | 3.691 | 0.0607 | 7.982 | 6.687 | 0.2328 | 0.1616 |
| CRHE2133 | Residual Feed Intake | 1427 | 0.086 | 0.054 | 0.1127 | 0.106 | 0.098 | 0.2778 | 0.2793 |
| CRHE2133 | Days on Feed | 1445 | 0.152 | 0.099 | 0.1245 | 0.255 | 0.179 | 0.1549 | 0.2848 |
| CRHE2133 | Backfat | 1427 | −0.008 | 0.005 | 0.1570 | −0.010 | 0.010 | 0.3005 | 0.3667 |
| CRHE2133 | Marbling | 1061 | 4.949 | 3.772 | 0.1898 | 2.753 | 6.915 | 0.6906 | 0.2819 |

TABLE 4-continued

Single marker associations

| Marker | Trait | DDFM | Estimate | StdErr | P-Value | Estimate | StdErr | P-Value | ProbF |
|---|---|---|---|---|---|---|---|---|---|
| CRHE2133 | Daily feed intake | 1445 | 0.101 | 0.105 | 0.3391 | 0.104 | 0.191 | 0.5859 | 0.6089 |
| CRHE2133 | Dressing Percent | 1445 | 0.063 | 0.074 | 0.3940 | −0.049 | 0.135 | 0.7163 | 0.2061 |
| CRHE2133 | Backfat Rate | 1427 | 0.000 | 0.000 | 0.4496 | 0.000 | 0.000 | 0.6359 | 0.7422 |
| CRHE2133 | Percent Choice | 1436 | 0.009 | 0.018 | 0.6353 | 0.008 | 0.033 | 0.8147 | 0.8768 |
| CRHE2133 | Average Daily Gain | 1445 | −0.005 | 0.017 | 0.7432 | −0.011 | 0.030 | 0.7176 | 0.9337 |
| UCN3E2270 | Live Weight | 1443 | 11.482 | 3.512 | 0.0011 | 13.184 | 5.981 | 0.0276 | 0.0038 |
| UCN3E2270 | Daily feed intake | 1443 | 0.296 | 0.101 | 0.0033 | 0.246 | 0.171 | 0.1512 | 0.0040 |
| UCN3E2270 | Backfat | 1425 | −0.015 | 0.005 | 0.0042 | −0.016 | 0.009 | 0.0615 | 0.0127 |
| UCN3E2270 | Hot Carcass Weight | 1443 | 6.341 | 2.351 | 0.0071 | 7.483 | 4.001 | 0.0616 | 0.0235 |
| UCN3E2270 | Average Daily Gain | 1443 | 0.040 | 0.016 | 0.0130 | 0.039 | 0.027 | 0.1472 | 0.0301 |
| UCN3E2270 | Residual Feed Intake | 1425 | 0.120 | 0.052 | 0.0204 | 0.063 | 0.088 | 0.4724 | 0.0104 |
| UCN3E2270 | Yield Grade | 1436 | −0.040 | 0.024 | 0.0955 | −0.035 | 0.041 | 0.3955 | 0.1771 |
| UCN3E2270 | Cuttability | 1436 | 0.090 | 0.056 | 0.1057 | 0.080 | 0.095 | 0.3994 | 0.2005 |
| UCN3E2270 | Rib eye area | 1443 | 0.091 | 0.057 | 0.1084 | 0.081 | 0.096 | 0.4037 | 0.2056 |
| UCN3E2270 | Days on Feed | 1443 | 0.113 | 0.095 | 0.2317 | −0.045 | 0.161 | 0.7816 | 0.0557 |
| UCN3E2270 | Feed conversion ratio | 1443 | 0.016 | 0.015 | 0.2942 | 0.008 | 0.026 | 0.7436 | 0.3958 |
| UCN3E2270 | Dressing Percent | 1443 | −0.070 | 0.071 | 0.3201 | −0.066 | 0.120 | 0.5857 | 0.5569 |
| UCN3E2270 | Marbling | 1056 | 2.757 | 3.618 | 0.4461 | −1.302 | 6.169 | 0.8328 | 0.2961 |
| UCN3E2270 | Percent Choice | 1433 | 0.012 | 0.017 | 0.5008 | −0.002 | 0.030 | 0.9491 | 0.4763 |
| UCN3E2270 | Backfat Rate | 1425 | 0.000 | 0.000 | 0.8607 | 0.000 | 0.000 | 0.6478 | 0.8550 |
| UCN3P232 | Rib eye area | 1450 | 0.193 | 0.065 | 0.0030 | 0.245 | 0.083 | 0.0034 | 0.0103 |
| UCN3P232 | Hot Carcass Weight | 1450 | 6.152 | 2.693 | 0.0225 | 6.497 | 3.463 | 0.0608 | 0.0668 |
| UCN3P232 | Live Weight | 1450 | 7.685 | 4.031 | 0.0568 | 7.764 | 5.183 | 0.1344 | 0.1411 |
| UCN3P232 | Yield Grade | 1443 | −0.046 | 0.028 | 0.0983 | −0.065 | 0.035 | 0.0681 | 0.1894 |
| UCN3P232 | Cuttability | 1443 | 0.105 | 0.064 | 0.0991 | 0.149 | 0.082 | 0.0691 | 0.1917 |
| UCN3P232 | Dressing Percent | 1450 | 0.118 | 0.081 | 0.1448 | 0.136 | 0.104 | 0.1921 | 0.3452 |
| UCN3P232 | Daily feed intake | 1450 | 0.157 | 0.115 | 0.1700 | 0.158 | 0.147 | 0.2855 | 0.3584 |
| UCN3P232 | Feed conversion ratio | 1450 | 0.020 | 0.017 | 0.2542 | −0.001 | 0.022 | 0.9818 | 0.0233 |
| UCN3P232 | Backfat Rate | 1432 | 0.000 | 0.000 | 0.2916 | 0.000 | 0.000 | 0.3373 | 0.5735 |
| UCN3P232 | Residual Feed Intake | 1432 | 0.058 | 0.059 | 0.3277 | 0.025 | 0.076 | 0.7434 | 0.2580 |
| UCN3P232 | Average Daily Gain | 1450 | 0.013 | 0.018 | 0.4652 | 0.024 | 0.023 | 0.2983 | 0.5141 |
| UCN3P232 | Days on Feed | 1450 | −0.077 | 0.108 | 0.4745 | −0.032 | 0.139 | 0.8165 | 0.4785 |
| UCN3P232 | Backfat | 1432 | −0.003 | 0.006 | 0.5590 | −0.005 | 0.007 | 0.5070 | 0.8018 |
| UCN3P232 | Marbling | 1061 | −0.225 | 4.187 | 0.9571 | −5.621 | 5.320 | 0.2909 | 0.0621 |

TABLE 4-continued

Single marker associations

| Marker | Trait | DDFM | Estimate | StdErr | P-Value | Estimate | StdErr | P-Value | ProbF |
|---|---|---|---|---|---|---|---|---|---|
| UCN3P232 | Percent Choice | 1441 | −0.001 | 0.020 | 0.9747 | −0.030 | 0.026 | 0.2444 | 0.0274 |
| UQCRC1P059 | Backfat Rate | 1426 | 0.000 | 0.000 | 0.0733 | 0.000 | 0.000 | 0.0677 | 0.1829 |
| UQCRC1P059 | Days on Feed | 1444 | 0.193 | 0.114 | 0.0898 | 0.258 | 0.137 | 0.0603 | 0.1696 |
| UQCRC1P059 | Feed conversion ratio | 1444 | 0.029 | 0.018 | 0.1066 | 0.026 | 0.022 | 0.2315 | 0.1906 |
| UQCRC1P059 | Rib eye area | 1444 | 0.110 | 0.069 | 0.1093 | 0.132 | 0.083 | 0.1131 | 0.2688 |
| UQCRC1P059 | Average Daily Gain | 1444 | −0.028 | 0.019 | 0.1489 | −0.038 | 0.023 | 0.1070 | 0.2694 |
| UQCRC1P059 | Yield Grade | 1437 | −0.029 | 0.029 | 0.3204 | −0.025 | 0.035 | 0.4885 | 0.4975 |
| UQCRC1P059 | Marbling | 1057 | 4.163 | 4.346 | 0.3383 | 3.585 | 5.240 | 0.4941 | 0.5366 |
| UQCRC1P059 | Cuttability | 1437 | 0.063 | 0.068 | 0.3522 | 0.052 | 0.082 | 0.5239 | 0.5320 |
| UQCRC1P059 | Dressing Percent | 1444 | 0.078 | 0.085 | 0.3602 | 0.176 | 0.103 | 0.0867 | 0.0398 |
| UQCRC1P059 | Residual Feed Intake | 1426 | 0.038 | 0.062 | 0.5383 | 0.009 | 0.075 | 0.9049 | 0.3818 |
| UQCRC1P059 | Hot Carcass Weight | 1444 | 1.532 | 2.846 | 0.5904 | 1.846 | 3.437 | 0.5912 | 0.8611 |
| UQCRC1P059 | Daily feed intake | 1444 | −0.043 | 0.122 | 0.7250 | −0.104 | 0.147 | 0.4800 | 0.5465 |
| UQCRC1P059 | Live Weight | 1444 | 1.124 | 4.263 | 0.7922 | −0.324 | 5.148 | 0.9498 | 0.6737 |
| UQCRC1P059 | Backfat | 1426 | 0.001 | 0.006 | 0.8953 | 0.005 | 0.007 | 0.5206 | 0.3587 |
| UQCRC1P059 | Percent Choice | 1434 | 0.000 | 0.021 | 0.9842 | −0.017 | 0.026 | 0.5031 | 0.1678 |
| UTS2RP372 | Rib eye area | 1441 | 0.163 | 0.060 | 0.0064 | 0.126 | 0.088 | 0.1491 | 0.0064 |
| UTS2RP372 | Backfat | 1423 | 0.008 | 0.005 | 0.1398 | 0.015 | 0.008 | 0.0624 | 0.1732 |
| UTS2RP372 | Cuttability | 1434 | 0.082 | 0.059 | 0.1639 | 0.029 | 0.086 | 0.7375 | 0.1073 |
| UTS2RP372 | Yield Grade | 1434 | −0.033 | 0.025 | 0.1941 | −0.010 | 0.037 | 0.7987 | 0.1213 |
| UTS2RP372 | Residual Feed Intake | 1423 | −0.069 | 0.054 | 0.2020 | −0.052 | 0.080 | 0.5166 | 0.3188 |
| UTS2RP372 | Dressing Percent | 1441 | 0.082 | 0.074 | 0.2671 | 0.131 | 0.109 | 0.2277 | 0.4766 |
| UTS2RP372 | Daily feed intake | 1441 | −0.102 | 0.106 | 0.3366 | −0.084 | 0.156 | 0.5881 | 0.5523 |
| UTS2RP372 | Average Daily Gain | 1441 | −0.016 | 0.017 | 0.3503 | −0.016 | 0.025 | 0.5184 | 0.6226 |
| UTS2RP372 | Days on Feed | 1441 | −0.081 | 0.099 | 0.4146 | −0.139 | 0.146 | 0.3389 | 0.6330 |
| UTS2RP372 | Backfat Rate | 1423 | 0.000 | 0.000 | 0.4617 | 0.000 | 0.000 | 0.2037 | 0.3635 |
| UTS2RP372 | Live Weight | 1441 | −2.133 | 3.710 | 0.5654 | −5.207 | 5.440 | 0.3387 | 0.5732 |
| UTS2RP372 | Feed conversion ratio | 1441 | −0.009 | 0.016 | 0.5713 | −0.009 | 0.023 | 0.7003 | 0.8384 |
| UTS2RP372 | Marbling | 1053 | 1.220 | 3.688 | 0.7409 | 0.436 | 5.589 | 0.9378 | 0.8858 |
| UTS2RP372 | Hot Carcass Weight | 1441 | −0.323 | 2.477 | 0.8963 | −1.771 | 3.633 | 0.6259 | 0.7704 |
| UTS2RP372 | Percent Choice | 1432 | 0.000 | 0.018 | 0.9875 | −0.012 | 0.027 | 0.6621 | 0.6983 |

Example 3

Association of UQCRC1 Promoter SNPs with Fat Deposition and Fatty Acid Composition In addition to beef marbling score (BMS) and subcutaneous fat depth (SFD) described above, the Wagyu×Limousin $F_2$ progeny was also measured for three estimated stearoyl-CoA desaturase activities designated as $R_1=(14:1/14:0)\times 100\%$, $R_2=(16:1/16:0)\times 100\%$ and $R_3=(18:1/18:0)\times 100\%$, relative amounts of saturated (SFA), monounsaturated (MUFA) and polyunsaturated fatty acids (PUFA), conjugated linoleic acid mg/100 g dry muscle (CLA), cholesterol mg/100 g dry muscle (CHOL), ribeye area (REA, in $in^2$) and percent kidney, pelvic and heart fat (KPH). The GLM (general linear model) analysis revealed that the bovine UQCRC1 gene was also associated with $R_2$, $R_3$, SFA, MUFA, PUFA, REA and KPH, respectively (Table 5).

TABLE 5

Associations of UQCRC1 gene with fat deposition and fatty acid composition*

| Phenotype | | g.13487C > T | | g.13671T > C | | g.13725A > G |
|---|---|---|---|---|---|---|
| R2 | CC | 14.45 ± 0.182$^a$ | CC | 14.94 ± 0.190$^a$ | GG | 14.67 ± 0.142$^a$ |
|  | CT | 14.62 ± 0.201$^a$ | CT | 14.40 ± 0.186$^a$ | GA | 14.70 ± 0.333$^a$ |
|  | TT | 15.82 ± 0.382$^b$ | TT | 14.85 ± 0.603$^a$ |  |  |
|  | $P_{GLM}$ | 0.0055 | $P_{GLM}$ | 0.1212 | $P_{GLM}$ | 0.9298 |
| R3 | CC | 371.3 ± 4.220$^a$ | CC | 389.0 ± 4.530$^a$ | GG | 381.6 ± 3.380$^a$ |
|  | CT | 374.6 ± 4.650$^a$ | CT | 370.1 ± 4.420$^b$ | GA | 361.3 ± 7.950$^b$ |
|  | TT | 423.9 ± 8.850$^b$ | TT | 361.7 ± 14.38$^{ab}$ |  |  |
|  | $P_{GLM}$ | <0.0001 | $P_{GLM}$ | 0.0063 | $P_{GLM}$ | 0.0200 |
| SFA | CC | 43.27 ± 0.192$^a$ | CC | 43.40 ± 0.201$^a$ | GG | 43.42 ± 0.148$^a$ |
|  | CT | 43.86 ± 0.212$^b$ | CT | 43.47 ± 0.196$^a$ | GA | 43.59 ± 0.349$^a$ |
|  | TT | 42.76 ± 0.403$^a$ | TT | 43.57 ± 0.638$^a$ |  |  |
|  | $P_{GLM}$ | 0.0249 | $P_{GLM}$ | 0.9496 | $P_{GLM}$ | 0.6658 |
| MUFA | CC | 50.40 ± 0.201$^a$ | CC | 50.53 ± 0.210$^a$ | GG | 50.37 ± 0.156$^a$ |
|  | CT | 50.02 ± 0.221$^a$ | CT | 50.36 ± 0.205$^a$ | GA | 50.48 ± 0.367$^a$ |
|  | TT | 51.62 ± 0.421$^b$ | TT | 49.29 ± 0.667$^a$ |  |  |
|  | $P_{GLM}$ | 0.0042 | $P_{GLM}$ | 0.2027 | $P_{GLM}$ | 0.7809 |
| PUFA | CC | 4.76 ± 0.119$^a$ | CC | 4.41 ± 0.122$^a$ | GG | 4.61 ± 0.091$^a$ |
|  | CT | 4.45 ± 0.131$^{ab}$ | CT | 4.66 ± 0.119$^a$ | GA | 4.32 ± 0.214$^a$ |
|  | TT | 4.17 ± 0.249$^b$ | TT | 5.19 ± 0.388$^a$ |  |  |
|  | $P_{GLM}$ | 0.0546 | $P_{GLM}$ | 0.0869 | $P_{GLM}$ | 0.4023 |
| REA | CC | 13.34 ± 0.143$^a$ | CC | 13.00 ± 0.147$^a$ | GG | 13.08 ± 0.107$^a$ |
|  | CT | 13.09 ± 0.157$^a$ | CT | 13.29 ± 0.143$^a$ | GA | 13.75 ± 0.255$^b$ |
|  | TT | 12.85 ± 0.297$^a$ | TT | 13.83 ± 0.461$^a$ |  |  |
|  | $P_{GLM}$ | 0.2390 | $P_{GLM}$ | 0.1292 | $P_{GLM}$ | 0.0160 |
| KPH | CC | 2.68 ± 0.035$^a$ | CC | 2.77 ± 0.035$^a$ | GG | 2.70 ± 0.026$^a$ |
|  | CT | 2.73 ± 0.038$^a$ | CT | 2.70 ± 0.034$^a$ | GA | 2.76 ± 0.063$^a$ |
|  | TT | 2.73 ± 0.072$^a$ | TT | 2.43 ± 0.110$^b$ |  |  |
|  | $P_{GLM}$ | 0.6768 | $P_{GLM}$ | 0.0281 | $P_{GLM}$ | 0.3111 |

*Each genotype is presented with LSM ± SE (least square means ± standard error) and means within a column without common superscripts are significantly different (P < 0.05) among three genotypes.

Example 4

Flow Charts for Tracking the Rearing of Livestock

Figure 4:
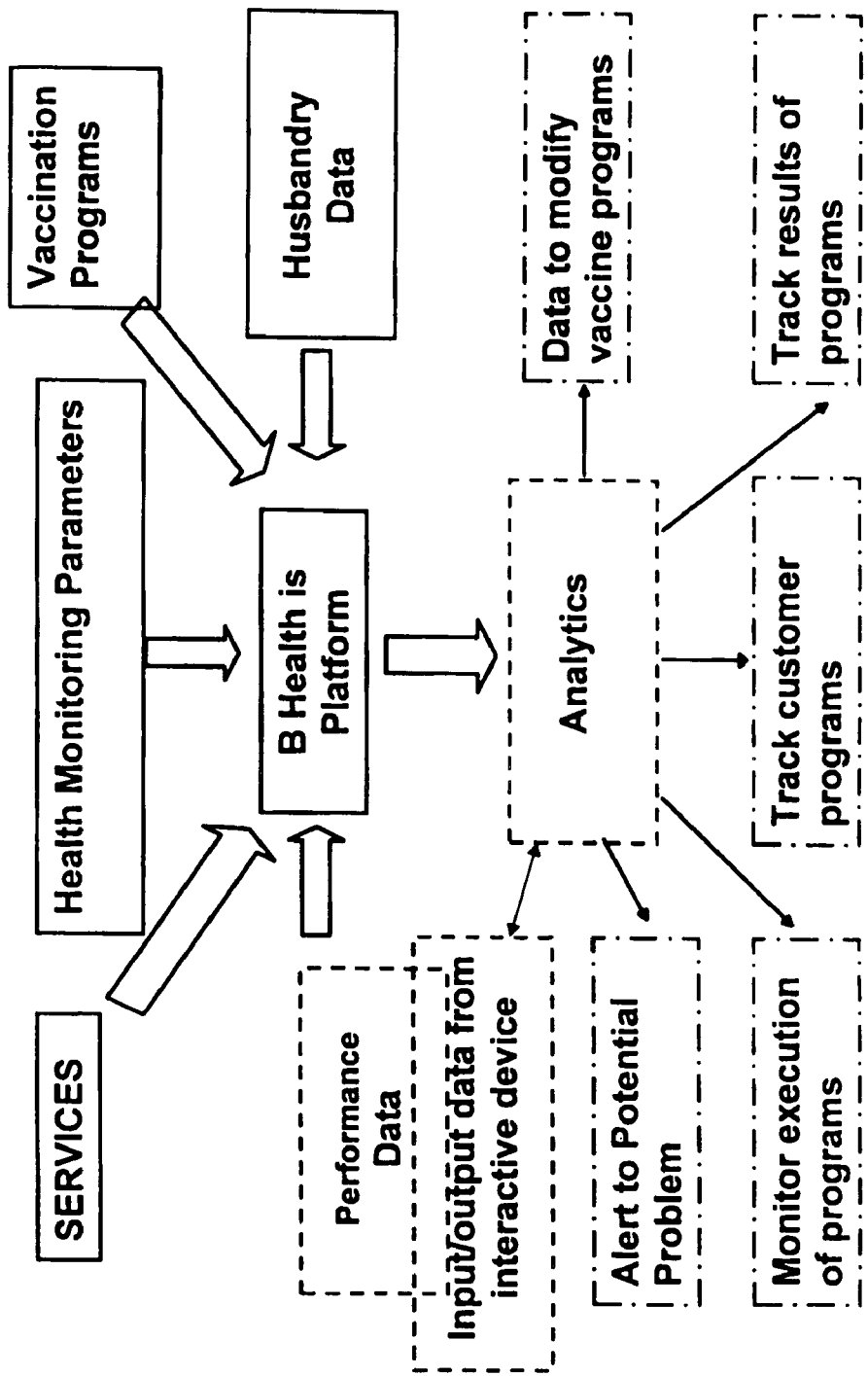
FIG. 4 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

FIG. 4 shows a flowchart of the input of data and the output of results from the analysis and correlation of the data pertaining to the breeding, veterinarian histories and performance requirements of a group of animals such as from bovines. The flowchart illustrated in FIG. 4 further indicate the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 5:
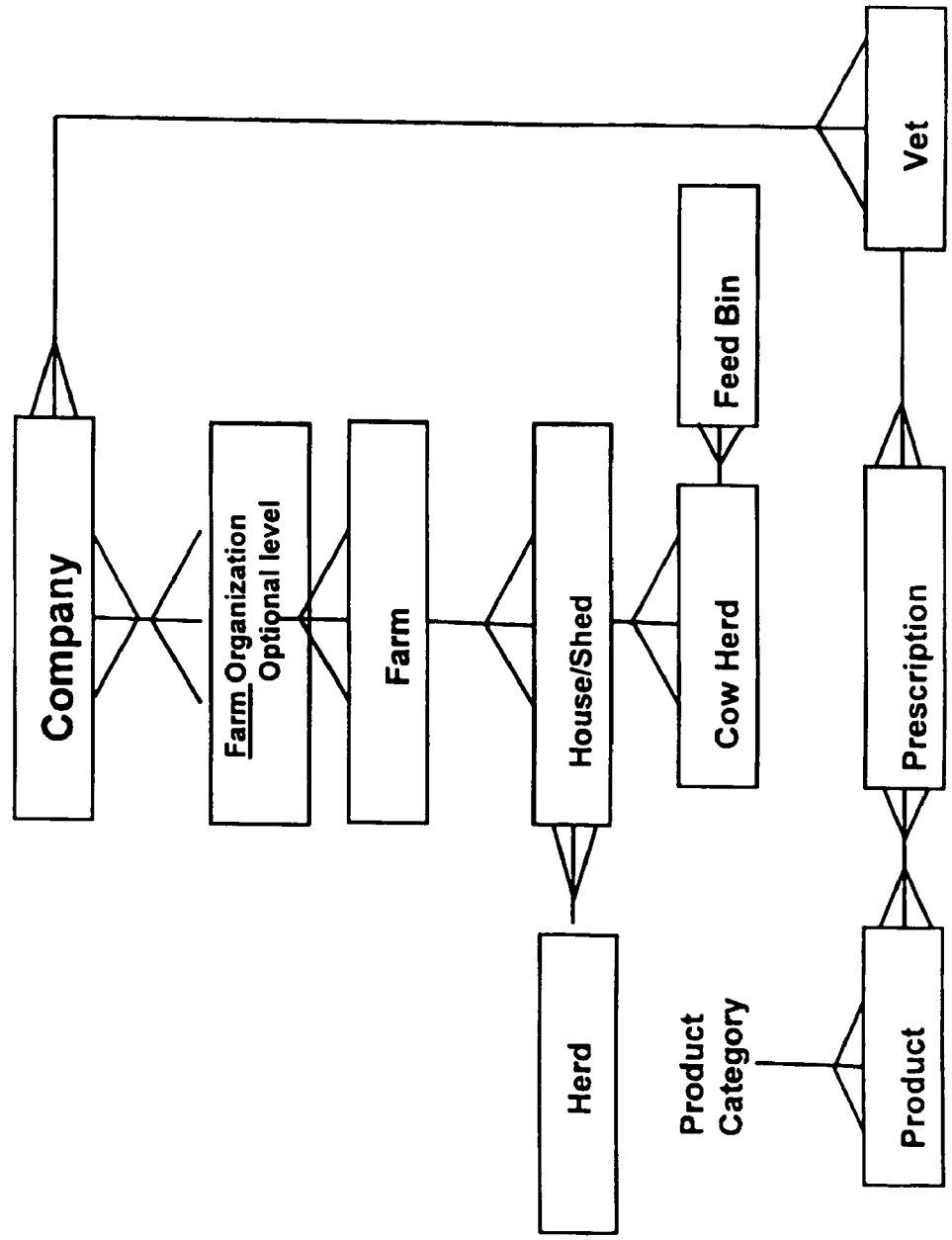
FIG. 5 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 5 illustrates potential relationships between the data elements to be entered into the system. Unidirectional arrows indicate, for example, that a house or shed is typically owned by only one farm, whereas a farm may own several houses or sheds. Similarly, a prescription may include have several veterinarian products.

Figure 6A:
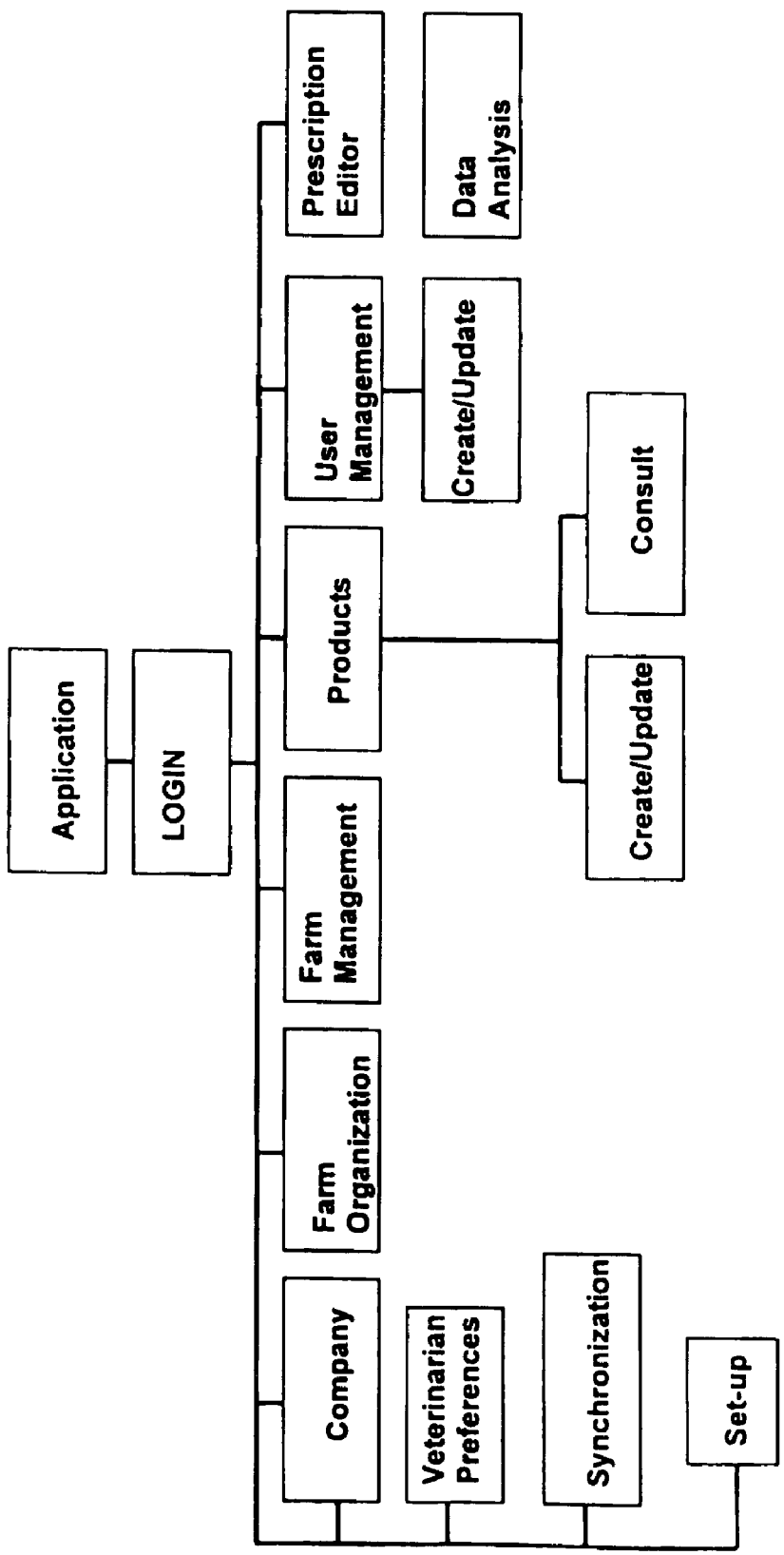
FIG. 6A illustrates the flow of events in the use of the portable computer-based system for data entry on the breeding and rearing of a herd of cows.
Figure 6B:
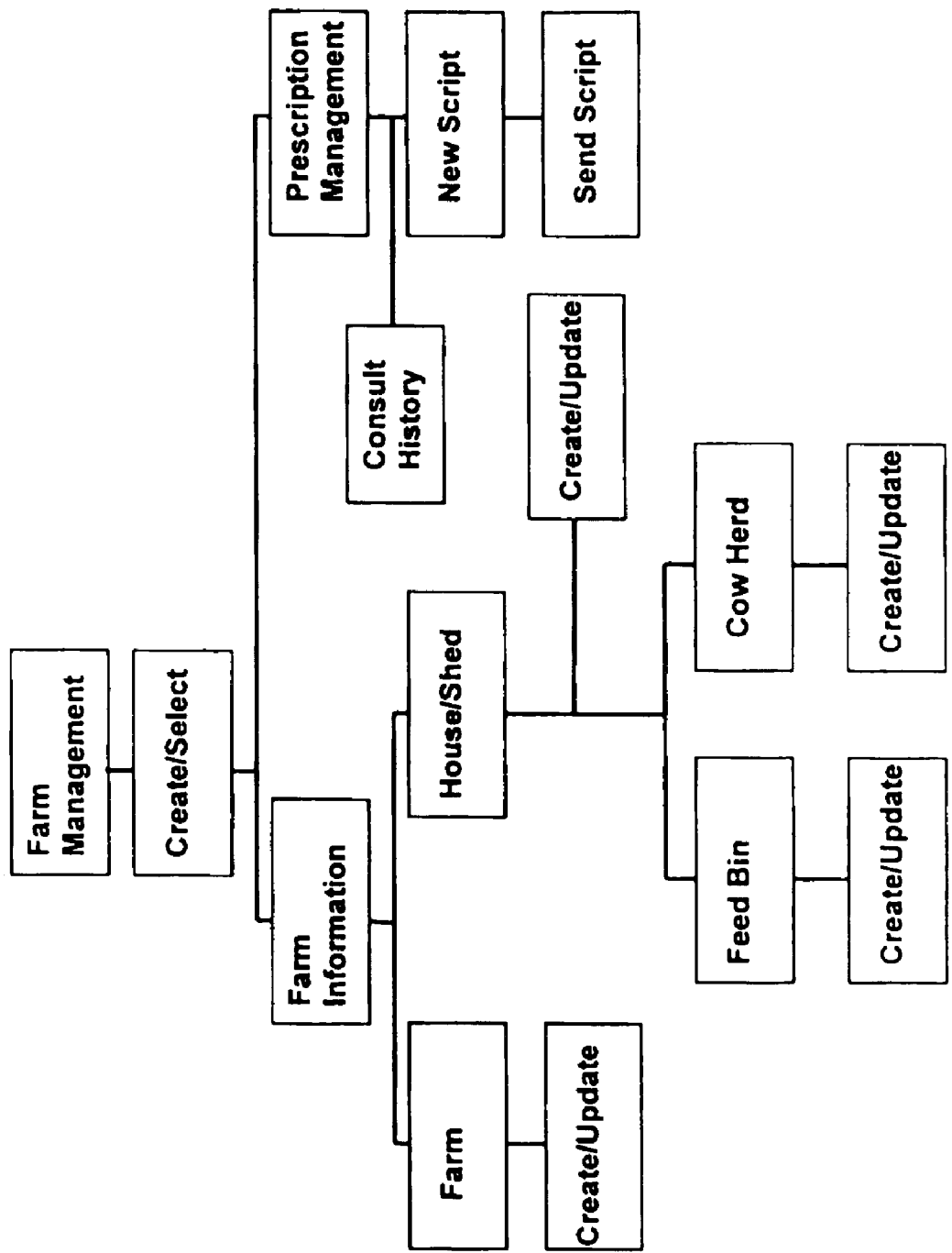
FIG. 6B illustrates the flow of events through the subroutines related to data entry concerning farm management.
Figure 6C:
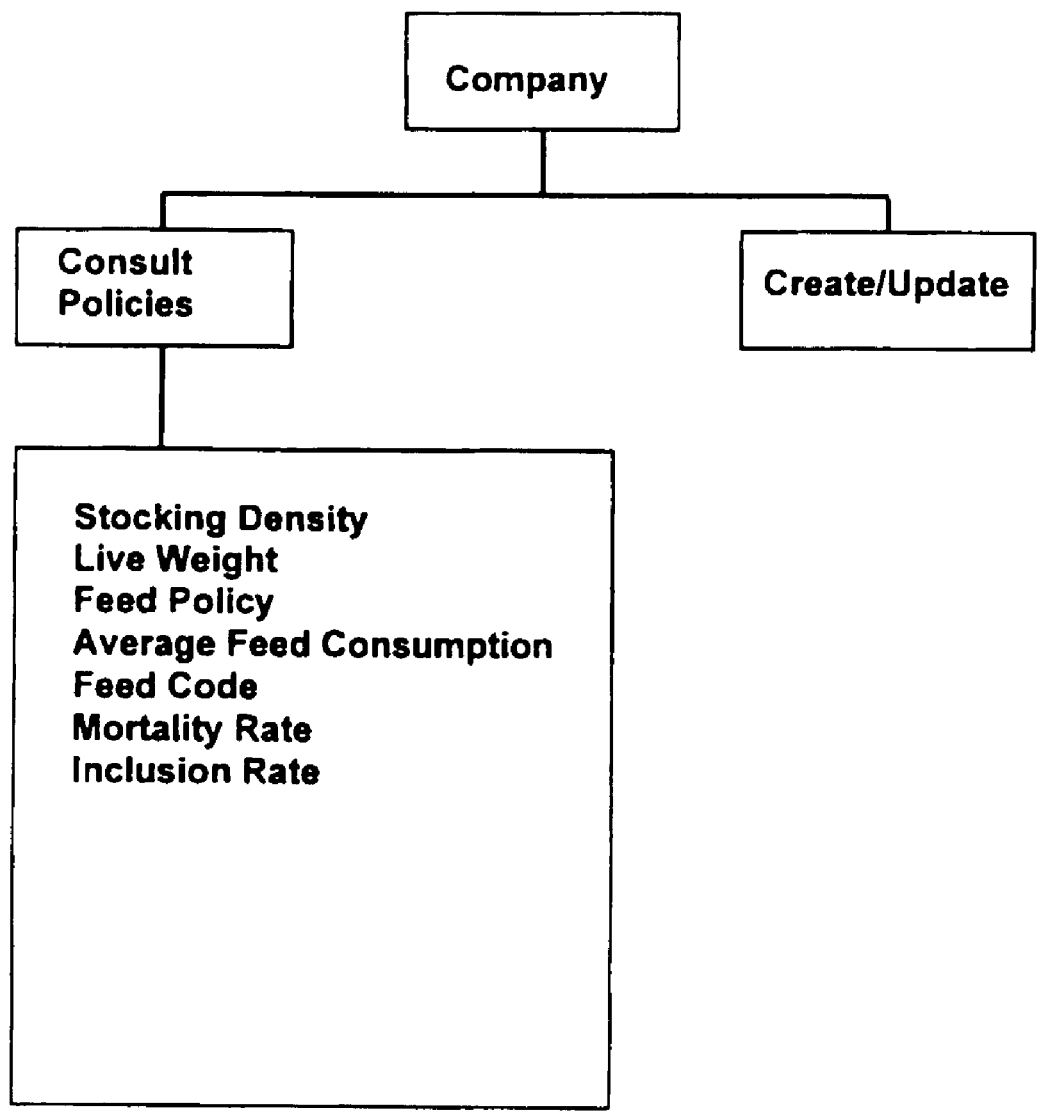
FIG. 6C illustrates the flow of events through the subroutines related to data entry concerning data specific to a company.

FIG. 6A illustrates the flow of events in the use of the portable computer-based system for data entry on the breeding and rearing of a herd of cows. FIG. 6B illustrates the flow of events through the sub-routines related to data entry concerning farm management. FIG. 6C illustrates the flow of events through the sub-routines related to data entry concerning data specific to a company.

Figure 7:
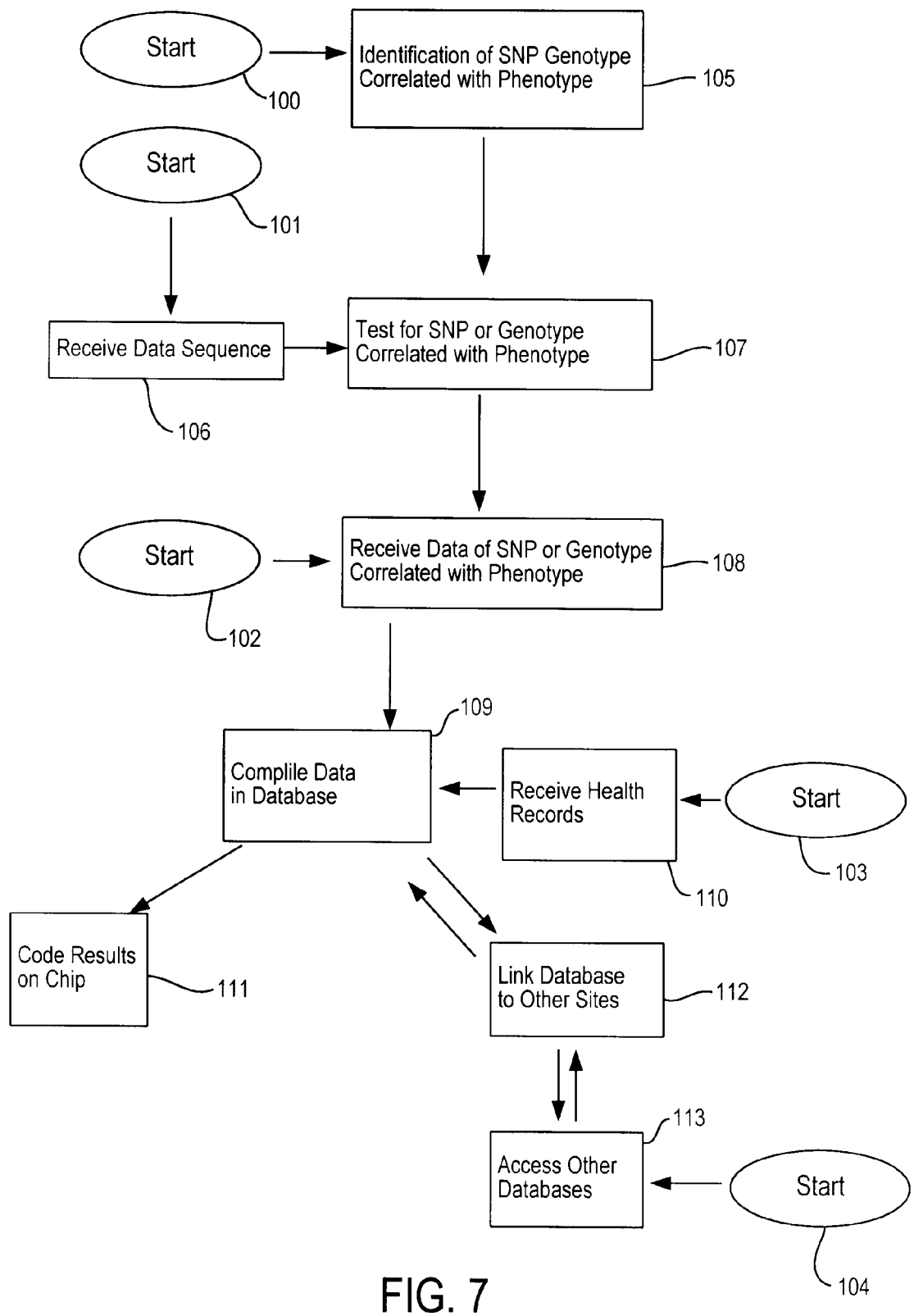
FIG. 7 illustrates a flow chart of the input of data and the output of results from the analysis and the correlation of the data pertaining to the breeding, veterinarian histories, and performance requirements of a group of animals.

FIG. 7 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub-grouping animals according to genotype wherein the animals of each sub-group have similar polymorphism in an UQCRC1 gene comprising:

(a) determining the genotype of each animal to be sub-grouped by determining the presence of single nucleotide polymorphisms in the UQCRC1 gene, and (b) segregating individual animals into sub-groups wherein each animal in a sub-group has similar polymorphisms in the UQCRC1 gene.

2. A method for sub-grouping animals according to genotype wherein the animals of each sub-group have similar genotypes in the UQCRC1 gene comprising:

(a) determining the genotype of each animal to be sub-grouped by determining the presence of single nucleotide polymorphisms of interest in the UQCRC1 gene, (b) segregating individual animals into sub-groups depending on whether the animals have, or do not have, the single nucleotide polymorphism(s) of interest.

3. The method of paragraphs 1 or 2, wherein the single nucleotide polymorphism(s) of interest is selected from the group, wherein the single nucleotide polymorphism(s) of interest is selected from the group consisting of the nucleotide substitutions defined in SNPs in the promoter of the UQCRC1 gene: AAFC03053028.1:g.13487C>T, g.13671 T>C, g.13709G>C and g.13725A>G.

4. A method for sub-grouping animals according to genotype wherein the animals of each sub-group have a similar genotype in the UQCRC1 gene comprising:

(a) determining the genotype of each animal to be sub-grouped by determining the presence of a nucleotide substitutions defined in SNPs in the promoter of the UQCRC1 gene: AAFC03053028.1:g.13487C>T, g.13671T>C, g.13709G>C and g.13725A>G, (b) segregating individual animals into sub-groups depending on whether the animals have, or do not have nucleotide substitution(s) defined in SNPs in the promoter of the UQCRC1 gene: AAFC03053028.1:g.13487C>T, g.13671T>C, g.13709G>C and g.13725A>G.

5. A method for identifying an animal having a desirable phenotype as compared to the general population of animals of that species, comprising determining the presence of a single nucleotide polymorphism(s) in the UQCRC1 gene of the animal, wherein the polymorphism is selected from the group comprising the nucleotide substitutions defined in in SNPs in the promoter of the UQCRC1 gene: AAFC03053028.1:g.13487C>T, g.13671T>C, g.13709G>C and g.13725A>G.

6. The method of paragraph 5, wherein the desirable phenotype is desirable beef marbling score (BMS) and subcutaneous fat depth (SFD), estimated stearoyl-CoA desaturase activities designated as $R_1=(14:1/14:0)\times100\%$, $R_2=(16:1/16:0)\times100\%$ and $R_3=(18:1/18:0)\times100\%$, relative amounts of saturated (SFA), monounsaturated (MUFA) and polyunsaturated fatty acids (PUFA), conjugated linoleic acid mg/100 g dry muscle (CLA), cholesterol mg/100 g dry muscle (CHOL), ribeye area (REA, in $in^2$) or percent kidney, pelvic and heart fat (KPH) or any combination thereof.

7. The method of any one of paragraphs 1 to 6 wherein the animal is a bovine.

8. The method of any one of paragraphs 1 to 7 wherein the UQCRC1 gene is a bovine UQCRC1 gene.

9. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

10. The method according to paragraph 9, wherein the computer system is an interactive system whereby modifications to the output of the computer-assisted method may be correlated according to the input from the interactive device.

11. The method according to paragraph 9 or 10, further comprising the steps of inputting into the programmed computer diagnostic data related to the health of the cow or herd of cows; and correlating the diagnostic data to the breeding and veterinary histories of the cow or herd of cows.

12. The method according to any one of paragraphs 9 to 11, wherein the veterinary data comprises a vaccination record for a cow or herd of cows.

13. The method according to any one of paragraphs 9 to 12 wherein the health data is selected from the group consisting of husbandry condition data, herd history, and food safety data.

14. The method according to any one of paragraphs 10 to 14, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

15. The method according to any one of paragraphs 9 to 14, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

16. The computer-assisted method according to any one of paragraphs 9 to 15 for optimizing efficiency of feedlots for livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

17. A method of transmitting data comprising transmission of information from such methods according to any one of paragraphs 9 to 15, selected from the group consisting of telecommunication, telephone, video conference, mass communication, a presentation, a computer presentation, a POWERPOINT™ presentation, internet, email, and documentary communication.

18. An interactive computer system according to any one of paragraphs 9 to 15 for tracking breeding and welfare histories of cows comprising breeding and veterinarian data corresponding to a bovine or herd of bovines, and wherein the computer system is configured to allow the operator thereof to exchange data with the device or a remote database.

19. The interactive computer system according to paragraph 18, wherein the input and output devices are a personal digital assistant or a pocket computer.

20. A method of doing business for tracking breeding and welfare histories of livestock comprising breeding and veterinarian data corresponding to one or more livestock animals comprising providing to a user the computer system of paragraph 18.

21. A method of doing business for tracking breeding and welfare histories of livestock comprising breeding and veterinarian data corresponding to one or more livestock animals comprising providing to a user the computer system of paragraph 19.

22. The method of doing business according to paragraph 20, further comprising providing the animal owner or customer with sample collection equipment, such as swabs and tags useful for collecting samples from which genetic data may be obtained, and wherein the tags are optionally packaged in a container which is encoded with identifying indicia.

23. The method of doing business according any one of paragraphs 9 to 15, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

24. The method of any one of paragraphs 7 to 23 wherein the data comprises presence or absence of one or more of a single nucleotide polymorphism(s) of interest in the UQCRC1 gene(s).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal having a thinner subcutaneous fat depth (SFD), a lower skeletal muscle lipid accumulation (SMLA), a lower estimated stearoyl-CoA desaturase 16:1/16:0×100% value (R2), a lower estimated stearoyl-CoA desaturase 18:1/18:0×100% value (R3), a lower amount of beef fat monounsaturated fatty acids (MUFA), or a combination thereof, said method comprising:
   (a) obtaining a biological sample from said bovine animal, said biological sample comprising nucleic acids encoding the bovine ubiquinol-cytochrome c reductase core protein I (UQCRC1) gene from said bovine;
   (b) detecting in said nucleic acids the presence of at least one of:
      (i) a C in at least one allele of the UQCRC1 gene at a position corresponding to 281 of SEQ ID NO: 1;
      (ii) a C in both alleles of the UQCRC1 gene at a position corresponding to 281 of SEQ ID NO: 1;
      (iii) a T in at least one allele of the UQCRC1 gene at a position corresponding to 465 of SEQ ID NO: 1; and
      (iv) a T in both alleles of the UQCRC1 gene at position corresponding to 465 of SEQ ID NO: 1; and
   c) correlating the presence of the nucleic acid content detected in step (b) with a thicker SFD, a higher SMLA, a higher R2, a higher R3, a higher beef fat MUFA, or a combination thereof in said bovine animal, wherein:
      the content detected in step (b)(i) is associated with lower R2, lower R3, and lower beef fat MUFA;
      the content detected in step (b)(ii) is associated with thinner SFD and lower SMLA;
      the content detected in step (b)(iii) is associated with lower R2, lower R3, and lower beef fat MUFA; and
      the content detected in step (b)(iv) is associated with thinner SFD and lower SMLA.

2. A method for identifying a bovine animal having a thicker SFD, a higher SMLA, a higher R2), a higher R3, a higher amount of beef fat MUFA, or a combination thereof, said method comprising:
   (a) obtaining a biological sample from said bovine animal, said biological sample comprising nucleic acids encoding the bovine UQCRC1 gene from said bovine;
   (b) detecting in said nucleic acids the presence of at least one of:
      (i) a T in both alleles of the UQCRC1 gene at a position corresponding to 281 of SEQ ID NO: 1
      (ii) a T in at least one allele of the UQCRC1 gene at a position corresponding to 281 of SEQ ID NO: 1
      (iii) a C in both alleles of the UQCRC1 gene at a position corresponding to 465 of SEQ ID NO: 1; and
      (iv) a C in at least one allele of the UQCRC1 gene at position corresponding to 465 of SEQ ID NO: 1;
   c) correlating the presence of the nucleic acid content detected in step (b) with a thicker SFD, a higher SMLA, a higher R2, a higher R3, a higher beef fat MUFA, or a combination thereof in said bovine animal, wherein:
      the content detected in step (b)(i) is associated with higher R2, higher R3, and higher beef fat MUFA;
      the content detected in step (b)(ii) is associated with thicker SFD and higher SMLA;
      the content detected in step (b)(iii) is associated with higher R2, higher R3, and higher beef fat MUFA; and
      the content detected in step (b)(iv) is associated with thicker SFD and higher SMLA.

* * * * *

SEQUENCE LISTING

<160> NUMBER OF SEQ ID NOS: 3

<210> SEQ ID NO 1
<211> LENGTH: 14768
<212> TYPE: DNA
<213> ORGANISM: Bos taurus

<400> SEQUENCE: 1

```
attcccaagt ggctcagtgg gtaaagaatc cacctacaat gcaggagata tgggttcaat      60
ccctgggtca ggaagatccc ctggaggagg aaatggcaac cagtccagta ttcttgcctg     120
gaaaatccca gtaacagaag agcctggtgg gctccagtcc atgtggttgc aaagagtcgg     180
acacgactga aatgactgcg cacgcacgca cgcacactgc tggaaggaag gtacaccgga     240
aggaattgtg tcacagcaag aggagcctaa gaaaacacga cagtgaaacg taatgtggtg     300
tcctggacag gatcctagaa caaaaaggc cattagatga aaaccaacta agggaatctg     360
aataaactat gaagtcaaag tcgctctgtc atgtccgact ctttgtgacc ccacggacta     420
tacagtccat ggaattctcc aggccagaat actggagtga gtagtctttc ctttctccag     480
ggtatcttcc caacccaggg atggatccca ggtctcccac aggcagattc tttaccagct     540
gagccccaag ggaagtccaa gaattttgca ctttagaaat aataaatgtg tcaatactga     600
ttcattaatt gtaacaaagt tatcagaata aggtaagata ttaataaggc aaattgtgca     660
tggctgtatg tgggcaggta tatatgggaa attctgtact ttctgctcag attttctgta     720
aatataaaat ggttctaaac accagtaatt aaaaaaactg tactaaaaaa ctaggagatt     780
ctatttcact gtattttttca tgtctagatg ataacgtcat tttagttcac aagatattaa     840
tcaatgcaca cttaagcatc atctctttga tgtttaacat aattttgttt attttttggct     900 gtgttgtgtc ttctttgctg tatggatttt ctctagctgc agtgagccag gctgctcctc     960
ctcgaggtgc tcgggcctct cgttgtggtg atgctctctt gttgcagagc aggggctcta    1020
gggtgtgggg gcttcaatag ttgtggcaca agggctctag agcagaggct caatagttgt    1080
ggttcagttc agttcagttc agtctctcag gtgtgtccga ctctttgcaa ccccatgaat    1140
cacagcacgc caggcctccc tgtccatcac catctcccag agttcactca aactcacatc    1200
catcgagtca gtgatgccat ccagccatct catcctctgt cgtcccctct tcctcctgcc    1260
cccaatccct cccatcatca gagtcttttc caatgagtca actctttgca tgaggtggcc    1320
aaagtgctgg aatttcagct ttagcatcat tccttccaaa gaaatcccag ggctgatctc    1380
ctttagaata gactggttgg atctccttgc agtccaaggg actctcaaga gatgggctta    1440
attgctcttt ggcatgtggg atcttcccag atgaggtttc aaaccggtgt cttctggact    1500
ggcaggtgga ttctttacca gtgagccacc agggaagccc cttctgtttc attttcataa    1560
aagaaagttc tattttcatt gagcgatatt ttgaaaggtc acaaaaaatc tcatatatct    1620
```

```
gtaaaaggaa gttcagttca gaaatatgcc attatttcaa aagcaacaaa tacttttaat    1680
aaaagtttta ttttactttt ttttttttt taatttctgg ccatgcacag tggcttgtag     1740
gatcttagtt acccaaccag ggattgaatc ccagccactg cagtgaaagc accgagtcct    1800
agccactgga ctgccagaga attccctaaa aatttaaaat catgtattaa aataaaacag    1860
aagtgtgaaa atggtagcct cttccccctt cccctgaatt tattttctgt aagtcatctg    1920
actgagactt tacagtgagt tcctaggaat tctctgttgc ctatgcaagt cctcttgatg    1980
tgtgttttgt tttccaaaca aggaatcttt tccacaaatt agtctctaaa attgttcctt    2040
ttttcttagc aacacattgc taaattcttt ccatgttaac catctgaatt tactccgttc    2100
ctttaaaaag aagaccgtga cttttcaaca gccgcccagc cgtcctaggt tccagcctgg    2160
tactttagcc ctgggggtga tagaattcca gttgagctat ttcaaatcct gaaggatgat    2220
gctgtgaaag tgctgcactc aatatgccag caaatttgga aaactcagca gtggccacaa    2280
gactggaaaa ggtcagtttt cattccaatc ccaaagaaag gcaatgccaa agaatgctca    2340
aactaccgca caattgcact catctcacac gctagtaaag taatgctcaa aattctccaa    2400
gccaggcttc agcaatacgt gaaccatgaa cttcctgatg ttcaagctgg ttttagaaaa    2460
ggcagaggaa ccagagatca aattgccaac atcggctgga tcatgaaaaa agcaagagag    2520
ttccagaaaa acatctattt ctgctttatt gactgtgcca aagcctttga ctgtgtggat    2580
cacaataaac tgtggaaaat tcttcaagag atgggaatac cagaccacct gacctgcctc    2640
ttgagaaatt tgtatgcagg tcaggaagca acagctagaa ctggacatgg aacagactgg    2700
ttccaaatag gaaaggagt acggcaaggc tgtatattgt caccctgttt atttaactta     2760
tatgcagagt acatcatgag aaacgctggg ctggaagaaa cacaagctgg aatcaagatt    2820
gccgggagaa atatcaataa cctcagatat gcagatgaca ccacccttat ggcagaaagt    2880
gaagaggaac tcaaaagcct cttgatgaaa gtgaaagtgg agagtgaaca agttggctta    2940
aagcgcaaca ttgagaaaat gaagatcatg gcatccggtc ccatcacttc atgggaaata    3000
gacggggaaa cagtggaaac agtgtcagac tttatttttc tgggctccaa aatcactaca    3060
gatggtgact gcagccatga aattaaagga cgcttactct tggaaggaaa gttatgacca    3120
acctagatag catattcaaa agcagagaca ttactttgcc aacaaaggtt cgtctagtca    3180
aggctatggt ttttcctgtg gtcatatatg gatgagagag ttggactgtg aagaaggctg    3240
agcgccaaag aattgatgct tttgaactgt ggtgttggag aagactcttg agagtccctt    3300
ggactgcaag gagatccaac cagtccattc tgaaggagat cagccctggg atttctttgg    3360
aaggaatgat gctaaagctg aaactccagt actttggcca cctcatgcga acagttgact    3420
cattggaaaa gactctgatg ctgggaggga ttggggcaa gagaggagaa ggggacgaca     3480
gaggatgaga tggctggatg gcatcactga ctcgatggac atgagtctga gtgaacttcg    3540
ggagttggtg atggacaggg aggcctggcg tgctgcggtt catgggtcg caaagagtcg     3600
gacacgacta agcgactgat ctgatctgat ctgcggttcg caaacatgct gtgcttcgc     3660
ttccggcccg ctcgcccact ccaagcactc agtgcagtcg aggcgcccac ggttcgtgag    3720
aaacgtcggg cactctccca cgagtgaagg ggaaagatga actggatgca gaacagatct    3780
gagcaggacg atgactagcc aggggcattg atgcgcgctg gtacccaggg acgcgaagac    3840
aagaagcagc gaccttcagg gagtaagtga atttttccgg tctcctccgc caggggggcgg   3900
ccgagcgcca agaccccagt actgcgcctg cgcctcgcgc ctctacgcat gcgtggcgcg    3960
```

```
gcccagcgtc cactggagct tagaagatgg cggcttccgc tgtttgccgg gcagctggcg    4020
ccgggacgcg agtgctgcta cgcacccgcc gctcggtgag gtggcaacga gagcgcagag    4080
ctgtgggaag cggggcttcg gaacgcggac cgggagcggg ctgttagtgc ccgtggagaa    4140
tggggaggtc gcggggtcag ggccgtggga aggtcacggc ccagggcgcg aacgggagtc    4200
tcgtagaccg cctgagcacg gggacgggga tcccacactg caggcctgca agctgaggcg    4260 tgaccccta ctctagtcct cagtcccggt cgccttttc caacagccgg ccctgctgag      4320
gtcgtctgac ttgaggggca ccgccaccta cgcccaggct ctccagagcg tgccagagac    4380
gcaggtcagc cagctggaca acgggctgcg agtggcctcg gagcagtctt cccagcctac    4440
ctgcacggtg agcggagtcc gctgtcagga gggcgcctcc atgttgggca cggcctcctt    4500
tcccaggtcg gggtgtgacc ttgggctcta tggtttgggt cagactctcc tcagtcaccc    4560
tgaggattga ccctcctact ccagtcgcga ttctaaccat gccttgactt cgtggaggca    4620
gttctcacta aaccaacact catttagcat gtgatgcctg ccaatcagga ggccaacccc    4680
cttttcagct ttttctttag cagcccatgg gattcagaga cttagatgac tgccagcctc    4740
atggcccaaa cttgtaatcc cttggctaga ttggaaatgt attgcaaaag aaaaccacgt    4800
gaaaattcca gttaaatgga taattttcct gaagattggc tcaaagatag atatcttggt    4860
taggtaaaca ggagagaaga ttctcaagag gcgatctctc tctctctcat tccacccca     4920 cccctctcc aagtggtttg attggtaaat tctttgagtt ttccaggaat aatgtcctgt     4980
gatgcaagtt gtgactgaac accgcaaaaa gtgatgggta gctttcttcc tacatgacac    5040
ctgtataagc tgacacacag cctgttaaga aaacttgacc gagaatgctg tatttcatgg    5100
acactaagat gcccagggct tcccaggtgg ctcagtggca aaagaaccca cctgctaata    5160
caggagacac aagagaaatg ggtttgatcc ctgggtcggg aagatccctt ggagaaggaa    5220
atggcaacac actgtggaat tcttgcctgg acatcccat ggcagaggag cctggcaggc    5280
tacagtccat ggggtcacaa agagtcggat gcgacttagc gactgagagc aaaaatgaaa    5340
caaaagatgc ccttgatctt aaggagcacc actgtgctca attgccagag aaagaatgct    5400
gccagttgta gtcaaggaat actatggatt acaaaatgca tctgttgaag gtgttagatg    5460
ggtagtagat gatgttcatg taagaattta tggtatatag gacatacatg aacgtctctt    5520
agtaaagcag atgtgagcat tttaaatcag ctacgataca aatagtagaa gattagatct    5580
gtgttaccat gggggtgagt agtgtgatgt gcatttcaca gcacacaagg aagctattac    5640
aattataaga atctctcatt gggtgccaag gtgcgttggc agtgttaggt gtccaggtct    5700
gattaaaaag attttttaag tatgaatgag cctcctcctt taatggcgaa agaacgcaat    5760
ctccaggaca aaaagacagg gtgtaatttt taggaaggag aaaaaaagtt gtttgcaagt    5820
gattagtagt ttgccgagaa gaaacaaaga atcaactgaa aagtgagact gaatttaaga    5880
attttctgca gtgatgggac aggtgaatgt gcagttagaa gctttcctgg aagtctcgtc    5940
accagcagaa accagagcag ggattagagg tgatgcagtg tgactagtca gtcagctggc    6000
acccgagcgt ccgacctcgg ggccttctga gaacgtcttc cccacctgga accgtgagcc    6060
cctgtctggg gcttgttctg gatcctgcag ggtcaggtgt gagtgggggc tggtgtctgt    6120
ttctttatta ccttttttgg tgatttcttg tccaggtggg ggtatggatt gatgctggca    6180
gccgttacga gactgagaag aacaacgggg ctggctactt tgtggagcat ctggctttca    6240
aggtgaggct cctaaagtcc tgcatctccc ctgtactgag ggcttcctgc tgtccctcct    6300
gagtatgctg gtcagaaaag ttagcctcct cacttaggac tgttagcaag ggggcagagg    6360
```

-continued

```
gaagcgatct ctgtctggct ttcctgggag acgccacgtg ggccaggcct ctcctgagtg    6420
agtgcctacc tggtaaaccc ctgcacaagg tccccagagc cagaaaaacc ccaaggagca    6480
tgggagcccc gctcttcacc agaagccagg cctgtgttgt ttgtctgcac ggacgtagaa    6540
ttgcggatgt acacatgcat tgtaacaagt ccagcaactt agttttttgta aaatgctgtg    6600 tatctctgac ttgtaaaatc gagtaggagc tttcatgagg atgagaacaa ccccttagcc    6660
atcctgtgtt tgcatggagt aaacaatgag tttctaaacg aatgaaaaaa atagagacga    6720 tacaggggttg gtgaggggtgt ggagcaggaa tgggcagcta gccagctcca gcgtcacaga    6780
tgtgtgtgtc agtctcagca cgtgggtgtg tgtcattgga cagcagttct cacacacaca    6840
cacgcaggac gaaggctgag ccccacagag gcccctggca cacacacaca gtcatacatg    6900
gtgtgaggga gagtggggag cagcgtcgcc tgagcacagt gtgagtccac ctgaccacgg    6960
ctgtcagtaa gcgtgggctg gtgaggtcag gctgccgtgg gcgctctgca gtcacatgcg    7020
ctcccccgag ctgtcccccc tcttggtgtg ggggtgctgg atttctggta acacttttgg    7080
gcatgccctt cttccctggc ccctggatgt ctccattctg tcgggccacg gtgctgtggc    7140
cttgaggagc ttaaggccta ctgagcactt ggtggcccca gactctgggc cctgcacccc    7200
agagtctttg ctgagggcgc tacctgtgga ccagtggtcc tgctgggact tcagcctatg    7260
aggatgcagg atcttgggct cccatgtggc tggttccagg gaacaaagaa tcggcctggc    7320
aatgcccttg gagaaggagt ggagagcatg ggggcccatc ttaatgccta cagcacccgg    7380
gagcacacgg cttactacat taaggcgtta tcaaaggact tgccaaaagg taagcctgga    7440
gggcagggct ggcatgcggt aggactcccc gggtgcagag gacaggcgct caggagcccc    7500
tggcctgact gaagaatggg gtgacccttta gagaagagcc ttgacaccaa gggggtcagg    7560 cctgggggggt ttatgctgtt actgtctcca cacctgtcct ccttgcaccc agctgtagag    7620
ctcctggccg acatcgtgca gaactgcagc ctcgaggact cccagattga aaggagcgg    7680 gacgtgatcc tgcaggagct gcaggagaat gacacatcca tgcgggacgt ggtcttcaac    7740
tacctgcatg ccacgcgcctt ccagggcaca cctctagccc agtccgtgga ggggcccagt    7800
gagaatgtca ggtgcgagct ggctggtcca gggggcaggt tgtcccctta ttggggcctg    7860
agcaggccac agccgcagga gtttgcattt acttggccaa gtgcctgtgc tgtttatttt    7920
cttaattcac acaactggag acatttttctg tgttgccaca tgttccccag gagtctttga    7980
atgtttgtgt ggtccccact caaattgtgg gctttgtttc catgtgtgtg tcttacgggt    8040
gctctggggg ggtccctcca cgtggctgct tgtcctctgg taggaggagc cctgccgctg    8100
cccctgaagc ccccatgtca gcccacaccc tccttggagg ggactccaag cctatcctga    8160
agttggacgt gagaggcccc agtgagggct gccctcttgg ccccagagtg gcaagtgcca    8220 gagatgggggc aaggatccgg tgaagctgag tctccttgtc tgtctcctcc gccccatttt    8280
gtgtgacccg catcactgcg gtctgggagc agtgttgacc ccttggcggt gtgtcttgca    8340
ggaagctgtc gcgggcagac ctgaccgagt acctcagccg gcattacaag gccccccgaa    8400
tggtgttagc agcagctgga ggtgagcagt gggctggttg aagccctgtg gtaatggggg    8460
ggtgggctgg gctgggctgc aaccttgatt agcagggcca ggtctcctgg ttctgactgt    8520
gggggatctt ccattcctgt ggaccctgtt ccctccctgt cctgtccttg aggggcgtga    8580
cctcggtcct gtgctctctg aggtgggggtg ggattctgct gggccacctg gggctgctgc    8640
tcgcgtttca tgcacgcctc agttggcctg ctgacctctg caggcctcag gactttctca    8700
```

```
gcctcacctg gtccttggag acgaaggttg aggctggggg agattcaggc ctccagcctg   8760
ttcctcttgg cctatgtggg aaaccggacg tcgaatggta gatggaaagt gccccgaaag   8820
gaaggcacgg tgtggtcagg ggattttgt gggggactca gaggttaggg tggagaaggc    8880
agtggcaccc tactcaagta ctcttgcctg gaaaatccca tggatggagg agtctggtag   8940
gctacagtcc atgggtcgc taagagttgg acacgactga gcgacttcac tttcactttt    9000
cacttccatg cattggagaa ggaaatggcc acctactcca gtgttcttgc gtgtagaatc   9060
ccagggacgg gggagccggt gggctgccat ctgtggggtc gcacagagtt ggacacgact   9120
gaaagcagca gcagaggtta gggaggtgct tttgaagtac ttgtcatttg aacagagagc   9180
tgaagagtgg tgggatttag ttacatgggg agcgggggt ctgcacggag gggcagagtg    9240
gtgtcacggg ctctgtgatt ggaggcttgc tctgctgcca tgtgggcttc cctggtggct   9300
ccgctgtaat gaatccacct gccagtgcag gagacgcagg tttgatcctt gggtcaagaa   9360
gatcccctgg agaaggaaat gcagcccacc ccagtattcg tgcctgaaaa aatcccatgg   9420
acacagaagc ctggtgggct acagtccatg gagtcgcaga gttggacaca acttagcaac   9480
tgaacaacag cagctgctgc catgtcgggg ccagagcgga agcaggtgga tgcagggagg   9540
gcttgtggca ggtgcctggt gggaggcggc aggaggaaga gaagcggatg aactcgaaac   9600
gggtttgtag atggaagcct gatagacatc tagccaggag gggacaggag cgggtcaggg   9660
atgccgcccc aacttacggc agctggctgg acgggagaga ctgataggag gagctcggct   9720
ggtgaccttg gggctagtga accaagagca gtttgagctc ctgacacatc agacctgcag   9780
gatctgaggt caaggaagga aagaataaaa ggcagaggca cctgcggcc tgtacctggg    9840 ggcgctgctt cctaccacag cacccactgg tcgaggggct ggggcagcgg aagccgctgg   9900
tggaggggag gtccagcaag ggcatgagac gtgagtttgt gacattgctg ctccatgtcc   9960
ctggcacagg gggccccaga gctagtcaca gccccgcgtg gcgcttcttt gtgccctctc  10020
acctgccagc cctacagaat ctgcttgagg aagggctgga ggggcgaggc aggacgggtg  10080
gcctcacgcc cagggcacca gtcttgtgtg tggtgctggt gagagtgcgt cacgtgcttc  10140
agcccggcgt gtgctgcttc ctcatggccg aggtggtggg agctgttggg ccctgggggt  10200
ctgccctgcc tgccgccgag ctggagtgag tctgtggagg ctcctcttcc ctcacctggt  10260
cctgatgtcc tgtcttgggg gttctcccat cgaggcagga catggggtcc tgcgcctctg  10320
tgtggcgtct caggcccggc tgaccgataa gcacgctgtc catctcggca gggctggagc  10380
accggcagct gctcgaccaa gcccagaagc acttcagcgg gctctccggg acatacgacg  10440
aggacgctgt gcctaccctc agtccgtgcc gcttcactgg cagtcaggtg ggtgggggtg  10500
ggtgggggtg gcactcccgc gggcctggct ctttcacgac tccggaggtg cctcggaagt  10560
tgggccgggg tcccgcgcct gctgcctccc aggcacacgt ggtgacgctc gcatgcacat  10620
gcccccagcc acacttggca cctttgctgt cgccagggcg gtctggctgt tcctcagctt  10680
tgccacgtcc cgtttcagat ctgccaccgt gaggacggcc tgcctctggc ccacgtggcc  10740
atcgcagtga aggggcctgg ctgggcccac ccggacaacg tggccctcca ggtggccaac  10800
gccatcattg gccactacga ctgcacctac ggtggcggag cggtgagtgg gccaggcggg  10860
gacctcggtt caggggagag gcgcagctgg gcggcgggcg gggacctcag ttcagggag    10920 aggcgcagct gggcggcagg cgctcatcct gcggggttcg ggggcaggtg gcagagagga  10980
gggcaggtgc tgaccaccct ggcccctggt agcacctgtc cagcccactg gcttccattg  11040
ctgcgaccaa caagctgtgc cagagtttcc agaccttcaa catctgctac gcagacaccg  11100
```

```
ggctgctggg cgcacacttc gtctgcgacc acatgagcat cgacgacatg atgttcgtcc    11160
tgcagggcca gtggtgagtg gcggccgctg ttgctggccc cggcgggcgg gaggcttggg    11220
gaccgcagcg tctctcagga tgacgcgcac ctgcccctgc cctaggatgc gcctgtgcac    11280
cagtgccaca gagagtgagg tgctccgggg caaaaacctc ctccgaaacg ccttggtgtc    11340
tcatctggat ggtgagtcct gcagcccgtgt ggcgaggggt ggggtgcgta cgggcagtga    11400
cagtcccagc tcgaccagtg ctcctgacca agaccggcaa ggatgacgtt ggcggtcaca    11460
tcgtgtccca ccactgcccc ttccccaggg gcctggggtt tcaggaccc cttgtgggtg    11520 ggcctgagaa gcccatgggt acaggtcagg ttgcacagat gaagattgtg gtctaggatc    11580
aggccgagtc agcacagaac cctggaggtt cggtgcgggc ctgtgagctt ccctcccct    11640 cgtaggcacc actcccgtgt gtgaggacat cggacgcagt ctcctgacgt acggccgccg    11700
catccccctg gccgagtggg aaagccggat tgcggtaaca gggccctggg gggagagggc    11760
tttgggagtc ttgagctggc tgacttgcag agggtggggc gttgaggcag actgctcctg    11820
tgggcgcccc agggtgtaac cggggggcag ggcagaggcg tgggtggctg tggggtgcct    11880
ggggcccgtg gaagcctgtg gccggggagc cctgccgctg ttccccttc gggtgcgggg    11940 tcagcccctc ggtgcgtggg gcggtcttgg tcgctggatg ctgttgactg gtccccaggg    12000
gccttgccac tcattgtgcc ctctgcgtca tcctgtagga ggtggacgcc agggtggtgc    12060
gtgaggtctg ctccaagtac ttctacgacc agtgcccggc agtggctgga tttggtgagt    12120
agccgctctc tggccgcctc ctcaggctgc tgtctgggcc tcccatctgc ctctgctttc    12180
cccctttccc caactttcat tgggagcagc aagttggggc ccccaagagg ctctgcccaa    12240
ctgcctggct gccaggagt tcttgctcag aaaacctgtc ctggcagctc cctgactccc    12300
tgccaaggtg cctccatcaa taccccacac ccgccaggta acggacacct ccgcatgtgg    12360
ggtggggctc cagaggccag agcgtgaagg ggcaggctca gcacccctg gaggaatgtt    12420 ctttaccctc tttccactaa agcctgcctt gtgctgctct gggcagctct gaatggggcg    12480
cggcgcgggg ccaggtgtcc ctgtaccaca caggtgcccc accctgacgc ccacccctct    12540
ccccacaggc cccattgaac agcttccaga ttataaccgg atccgtagtg gcatgttctg    12600
gctgcgcttc taggcaggaa gcctgtgcag gcgagggcgg ggccggggtt cgaggttccc    12660
cccccacaaa cacaccacct cggtccttca gacctgtgca gctgctgact caccaaccaa    12720
taaagtcttg catcgagaac tgcgttgtcc ctctctcgtc cttggcgtgg agtccccggg    12780
ccatggtggg ggagcaggga cttccctcgg gtctgcgtgt cctggacgct ctgccttccc    12840
acaggctgat gtgtccttag tcaggggcga gcgtgggggg ctgtagcctg gaggccggaa    12900
gcctttgatg cctgcgggga gctgaggcca gctgtttgca gttagccaca tggggatgc    12960 tcctcaccag cctgtcctag agagggggtg tgggggacca tgggaactgc agcccagcc    13020 tttaccctgc tagggctccc agcctaggga ttgaggtggg aagcccttg ctgtgggtcc    13080 tggggggtcac cctctggggg accctggacc ccccagacc aggagagccc aagaaatgtc    13140
ctcgaggaag ccgcctctgt gtgtttactc tggattctgg gaggaggata gcccgaggca    13200
tagtgttccc atttggcttc tcactgctgc ctggacaggc aaggcaagaa tcctttgcct    13260
cgatttgccg ctgactcagg ctctaagaat atccctgagc tcagtgggc ctgagccccc    13320 tccctcgacg cgctctgtcc caggcaagtc ctgagctgct ggcctggcag tcccctcccc    13380
gtctgctgag gacctgctgg agctcacagc tgtctagtcc ccttgccacc tctgggctcc    13440
```

```
ggtccccaag gcaggagggc agataggccc tcttcctgtc cccccaccct tccagtcagg    13500
gttcctggga gcccactgtg gggtggatgg aagtgtgggc cagtttgcct gtgagggagg    13560
tggtgctgcc agtggtggac agggttctgg gacgaagtct gctgagaagg cggctattca    13620
gaagtgtcca gagcacccac agttcactcc caccgccccg gtttcctctc ccttaccctg    13680
tgtgttgcca tggctgcctg ctgtcccacg tttgagcccc gggaggatgg gccttggttt    13740
gtctgctaag cccaggcctg gtcctcaaag gccacaggtg cgctggacac agcaggcaag    13800
ctccctaggg tgacgtggtc ctagtgggcc ttgcagacct agccagggag tttgatctct    13860
cctccggagc cgtactgagg gagatgtatt gagggttact gggaagagga gtgacttgct    13920
cagctgacag cctggggact caggagcatt tcagtgtggt cccggtgagc cagcactgtg    13980
gcagctctag taagaaaggg cctgggctgt gggggcaca ggctagacag catcccagc     14040 agggctgggg taccacagag gacgggtggg ttggaggaag atgacctgcc cagctttggc    14100
tgccgttctg aggaatttgg aagtgtctta agacagtggg atgtgtgggg tgaaaccccc    14160
caaaagaggc cccagatgga gacatacggt gcagagactg aagtagagaa ggaaatgtcc    14220
aggggagtgt aggagggaga aaaagacctc tagggcccca ctgcccagat ggagggagct    14280
ggtttctggg gctgggccct aggctgtgtg cctgccagga ggctggagcc aggggcctca    14340
gagggccaca cccctgctcg tgagcttccc gggagcacca gacaggcacg cgtctgcaac    14400
ctaccttcca ccaacaacct ctcctcccag cctttgagtg accccctca cagcaggctg     14460 cccttccttt tggggggtca ctcatggttc tgataagatg gacacctgtt cacctgttcc    14520
tccaatctcc cctaaaggcc agacccaaat gtgtgtgtgt ctacactgtg taccagccct    14580
gctctgcaca gccacccttc cgtgcgagaa ggggtaaggg tcttgaggcg gggctgcctc    14640
tgtaatgaga gcctgtctgg ttctctgcag ccctcaccta taggacctat gggacggagg    14700
acttggtgat ccttggatgt ggctgagaag atcttcacct tgggaaaagg ttctgcgccc    14760
tacgggtc                                                            14768
```

<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
gaaggaaggt acaccggaag gaata                                         25

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
taaggcaaat tgtgcatggc tgta                                          24